United States Patent
Kito et al.

(10) Patent No.: US 7,737,427 B2
(45) Date of Patent: Jun. 15, 2010

(54) RADIATION IMAGE CAPTURING SYSTEM

(75) Inventors: Eiichi Kito, Kanagawa (JP); Tsuyoshi Tanabe, Kanagawa (JP); Takuya Yoshimi, Kanagawa (JP); Takeshi Kuwabara, Kanagawa (JP); Kazuharu Ueta, Tokyo (JP); Makoto Iriuchijima, Gunma (JP); Yasunori Ohta, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/219,807

(22) Filed: Jul. 29, 2008

(65) Prior Publication Data

US 2009/0032744 A1 Feb. 5, 2009

(30) Foreign Application Priority Data

Jul. 30, 2007 (JP) .............................. 2007-197950
Jul. 1, 2008 (JP) .............................. 2008-172108

(51) Int. Cl.
*G01N 23/04* (2006.01)
*G01T 1/24* (2006.01)
*H05G 1/64* (2006.01)
*A61B 6/08* (2006.01)

(52) U.S. Cl. ................. 250/580; 250/370.08; 378/98.8; 378/205

(58) Field of Classification Search ................. 250/580, 250/589, 591, 370.08, 370.09, 484.4; 378/98.8, 378/162, 165, 205, 207
See application file for complete search history.

(56) References Cited

U.S. PATENT DOCUMENTS 5,751,788 A * 5/1998 Khutoryansky et al. ..... 378/197
6,282,264 B1 * 8/2001 Smith et al. .................. 378/189
6,452,150 B1 * 9/2002 Mori et al. ............... 250/208.1
6,821,017 B1 * 11/2004 Tankersley .................. 378/207
7,046,764 B1 * 5/2006 Kump ......................... 378/117
7,127,032 B1 * 10/2006 Kump ......................... 378/117
2006/0261296 A1 * 11/2006 Heath et al. ................. 250/580
2007/0023667 A1 2/2007 Watanabe

FOREIGN PATENT DOCUMENTS

| JP | 07-140255 | 6/1995 |
|---|---|---|
| JP | 2000-105297 | 4/2000 |
| JP | 2003-172783 | 6/2003 |
| JP | 2006-305105 | 11/2006 |
| JP | 2007-20679 | 2/2007 |

* cited by examiner

*Primary Examiner*—David P Porta
*Assistant Examiner*—Faye Boosalis
(74) *Attorney, Agent, or Firm*—Jean C. Edwards, Esq.; Akerman Senterfitt

(57) ABSTRACT

A signal detector detects signals transmitted from signal generators disposed in a radiation detecting cassette, and a distance calculator calculates the distance between a radiation source and a radiation detector based on the signals detected by the signal detector. A determining unit determines whether the detected distance matches a predetermined distance from the radiation source to the radiation detector when a radiation image is captured. If the detected distance does not match the predetermined distance, the determining unit outputs, to a warning unit, a warning signal indicating that the detected distance does not match the predetermined distance, and also outputs a control signal for equalizing the detected distance with the predetermined distance, to a radiation source movement controller.

14 Claims, 16 Drawing Sheets

RADIATION IMAGE CAPTURING SYSTEM

CROSS-REFERENCE TO RELATED APPLICATIONS

The present application claims priority from Japanese Patent Application Nos. 2007-197950, filed Jul. 30, 2007, and 2008-172108, filed Jul. 1, 2008, the contents of both of which are herein incorporated by reference in their entirety.

BACKGROUND OF THE INVENTION

1. Field of the Invention

The present invention relates to a radiation image capturing system having a radiation conversion panel for detecting a radiation that has passed through a subject and converting the detected radiation into radiation image information.

2. Description of the Related Art

In the medical field, there have widely been used radiation image capturing apparatus which apply a radiation to a subject and guide the radiation that has passed through the subject to a radiation conversion panel, which captures a radiation image from the radiation. Known forms of the radiation conversion panel include a conventional radiation film for recording a radiation image by way of exposure, and a stimulable phosphor panel for storing radiation energy representing a radiation image in a phosphor and reproducing the radiation image as stimulated light by applying stimulating light to the phosphor. The radiation film with the recorded radiation image is supplied to a developing device to develop the radiation image, or the stimulable phosphor panel is supplied to a reading device in order to read the radiation image as a visible image.

In an operating room or the like, it is necessary to read a recorded radiation image immediately from the radiation conversion panel after the radiation image has been captured, for the purpose of quickly and appropriately treating the patient. As a radiation conversion panel that meets such a requirement, there has been developed a radiation detector having a solid-state detector for converting radiation directly into electric signals, or for converting radiation into visible light with a scintillator and then converting the visible light into electric signals, so as to read the detected radiation image.

In a radiation image capturing system which employs a radiation detecting cassette housing a radiation conversion panel therein, for accurately capturing a radiation image, the capturing of the radiation image is preceded by the transmission of image capturing conditions for an area to be imaged from the radiation detecting cassette through a communication cable (see Japanese Laid-Open Patent Publication No. 2003-172783) or the positioning of the radiation source and the radiation detecting cassette with respect to each other (see Japanese Laid-Open Patent Publication No. 2006-305105 and Japanese Laid-Open Patent Publication No. 2007-020679).

According to Japanese Laid-Open Patent Publication No. 2003-172783, though a radiation source can recognize the area of a subject (patient) to be imaged from the image capturing conditions transmitted from the radiation detecting cassette, the radiation source is unable to determine whether the distance between the radiation source and the radiation detecting cassette matches a predetermined distance (source-to-image distance, hereinafter also referred to as "SID") from the radiation source to the radiation detecting cassette at the time a radiation image of the subject is to be captured. Therefore, if the radiation image is captured when the distance between the radiation source and the radiation detecting cassette does not match the SID, then highly accurate radiation image information cannot be produced.

According to Japanese Laid-Open Patent Publication No. 2006-305105 and Japanese Laid-Open Patent Publication No. 2007-020679, a surgeon or a radiological technician visually checks if the distance between the radiation source and the radiation detecting cassette matches the SID or not by seeing the graduations on a measure mounted on the radiation source, after which the surgeon or the radiological technician manually position the radiation source and the radiation detecting cassette with respect to each other to equalize the distance between the radiation source and the radiation detecting cassette with the SID. Though the patient needs to be treated quickly and adequately, the visual checking and the manual positioning procedure tends to pose an undue burden on the surgeon or the radiological technician, who may possibly fail to capture a radiation image of the patient efficiently.

SUMMARY OF THE INVENTION

It is an object of the present invention to provide a radiation image capturing system which is capable of efficiently capturing a radiation image and producing highly accurate radiation image information.

A radiation image capturing system according to the present invention comprises a radiation source for outputting a radiation, a radiation detecting cassette housing therein a radiation conversion panel for detecting the radiation that has passed through a subject and converting the detected radiation into radiation image information, a distance detecting unit for detecting a distance between the radiation source and the radiation detecting cassette, and a determining unit for determining whether or not the detected distance matches a predetermined distance (SID) from the radiation source to the radiation detecting cassette when a radiation image of the subject is captured.

With the above arrangement, the distance detecting unit automatically detects the distance between the radiation source and the radiation detecting cassette, and the determining unit automatically determines whether the detected distance matches the predetermined distance or not. Before the radiation image is captured, therefore, the detected distance can be adjusted to the predetermined distance easily and highly accurately for producing highly accurate radiation image information.

Even if a surgeon or a radiological technician manually adjusts the detected distance before the radiation image is captured, since the distance is automatically detected and automatically checked against the predetermined distance, the burden on the surgeon or the radiological technician is greatly reduced for efficiently capturing radiation images.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
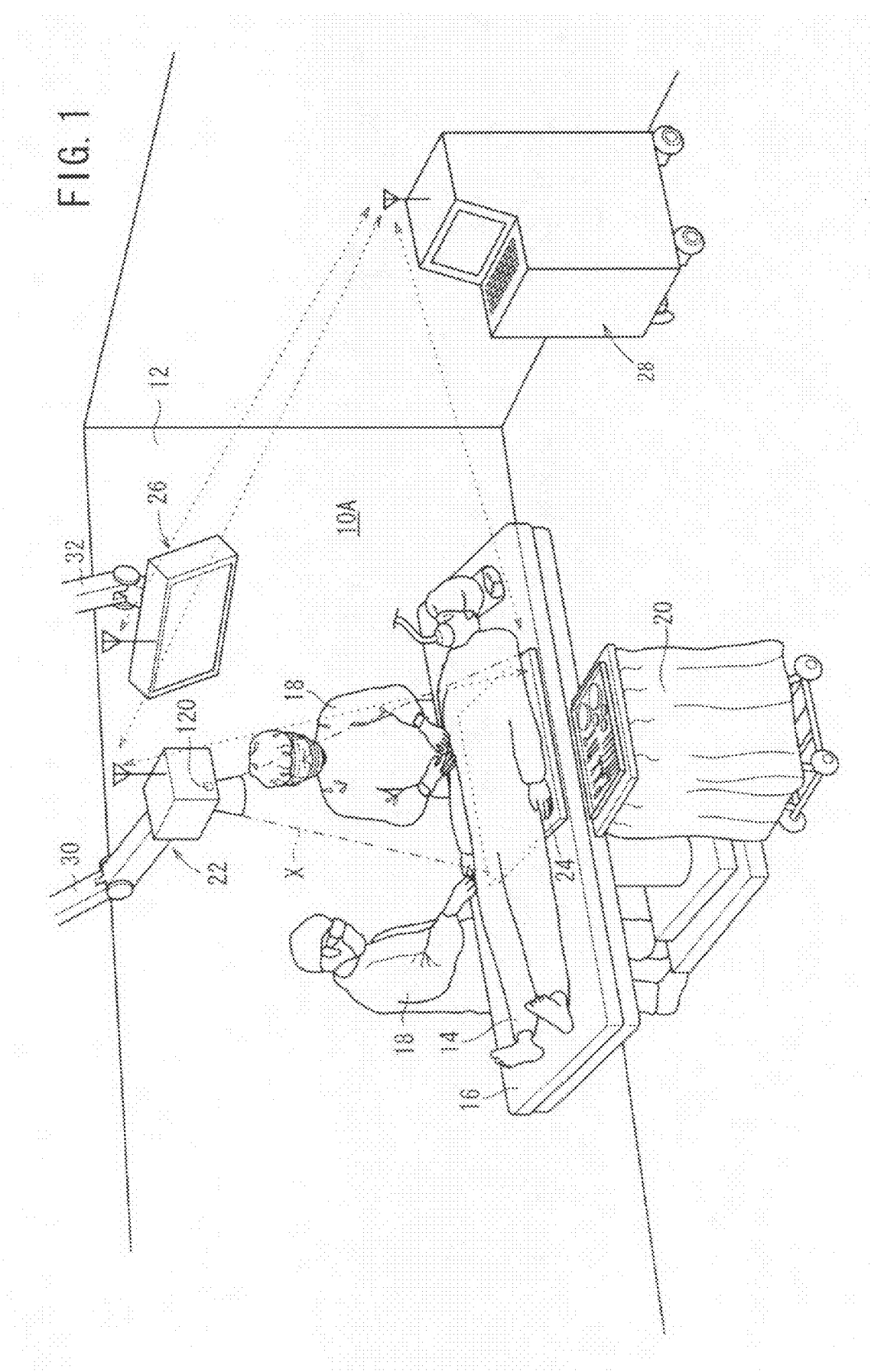
FIG. 1 is a perspective view of an operating room incorporating a radiation image capturing system according to a first embodiment of the present invention.

Like or corresponding parts are denoted by like or corresponding reference characters throughout views.

As shown in FIG. 1, an operating room 12 incorporates a radiation image capturing system 10A according to a first embodiment of the present invention. The operating room 12 has, in addition to the radiation image capturing system 10A, a surgical table (bed) 16 for a patient 14 to lie thereon, and an instrument table 20 disposed on one side of the surgical table 16 for placing thereon various tools and instruments to be used by surgeons 18 operating on the patient 14. The surgical table 16 is surrounded by various apparatus required for performing surgical operations, including an anesthesia apparatus, an aspirator, an electrocardiograph, a blood pressure monitor, etc.

The radiation image capturing system 10A includes an image capturing apparatus 22 for irradiating the patient 14 as a subject with radiation X at a dose according to image capturing conditions, a radiation detecting cassette 24 housing therein a radiation detector 40 (see FIGS. 2 through 6) for detecting radiation X that has passed through the patient 14, a display device 26 for displaying a radiation image based on radiation X detected by the radiation detector 40, and a console (controller) 28 for controlling the image capturing apparatus 22, the radiation detecting cassette 24, and the display device 26. The image capturing apparatus 22, the radiation detecting cassette 24, the display device 26, and the console 28 send and receive signals by way of UWB (Ultra Wide Band) wireless communications indicated by the broken lines.

The image capturing apparatus 22 is coupled to a universal arm 30 so as to be movable to a desired position for capturing images at a desired area of the patient 14 and also to be retractable to an out-of-the-way position while the surgeons 18 are performing a surgical operation on the patient 14. Similarly, the display device 26 is coupled to a universal arm 32 so as to be movable to a position where the surgeons 18 can easily confirm a captured radiation image displayed on the display device 26.

Figure 2:
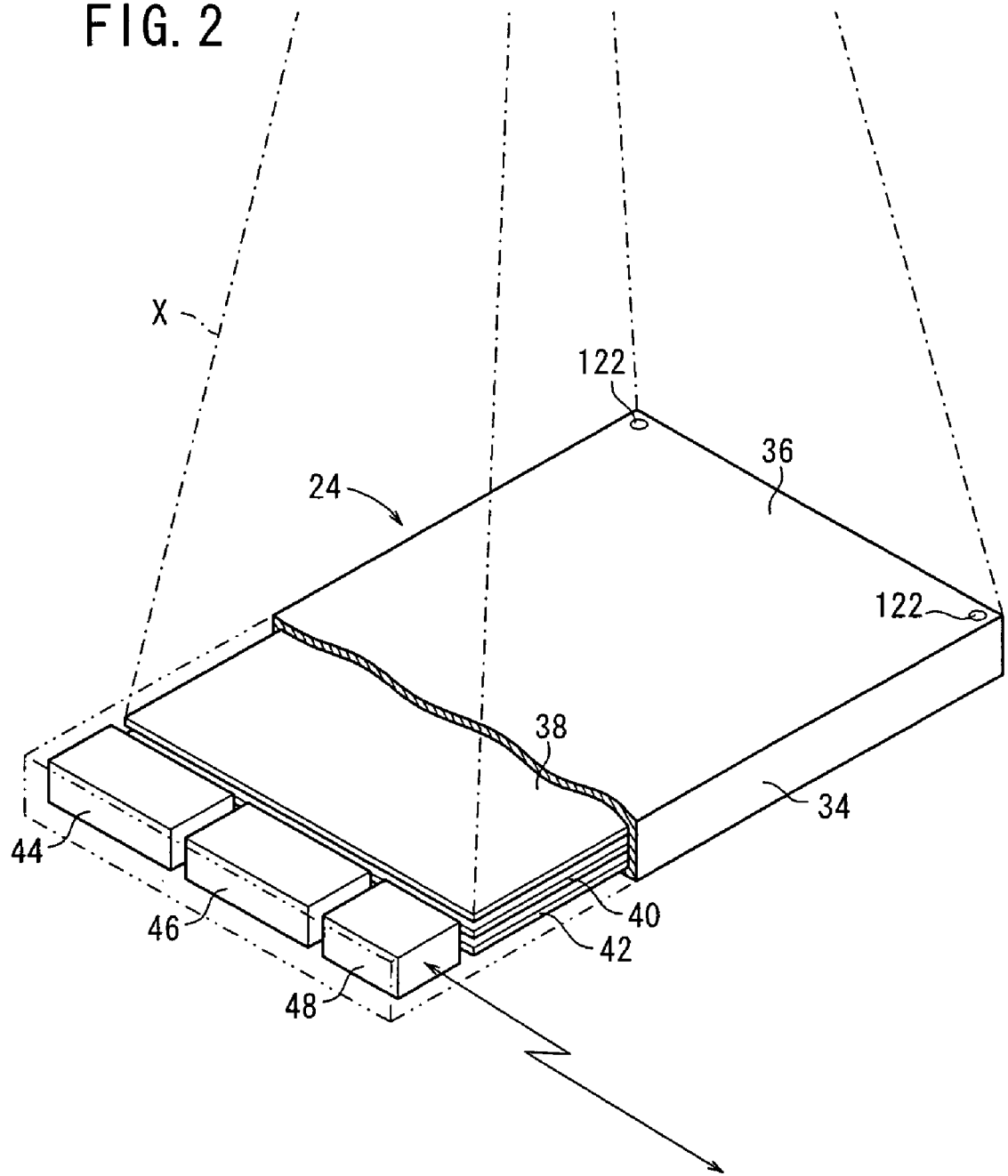
FIG. 2 is a perspective view, partly cut away, showing internal structural details of a radiation detecting cassette used in the radiation image capturing system shown in FIG. 1.

FIG. 2 shows in perspective the internal structural details of the radiation detecting cassette 24. As shown in FIG. 2, the radiation detecting cassette 24 has a casing 34 made of a material that is permeable to radiation X. The casing 34 houses therein a grid 38 for removing scattered rays from the radiation X from the patient 14, a radiation detector (radiation conversion panel) 40 for detecting radiation X that has passed through the patient 14, and a lead plate 42 for absorbing back scattered rays from the radiation X. The grid 38, the radiation detector 40, and the lead plate 42 are successively arranged in that order from an irradiated surface 36 of the casing 34, which is irradiated with radiation X. The irradiated surface 36 of the casing 34 may also be constructed so as to form the grid 38.

The casing 34 also houses therein a battery 44, which makes up a power supply for the radiation detecting cassette 24, a cassette controller 46 for energizing the radiation detector 40 with electric power supplied from the battery 44, and a transceiver (first wireless communication unit) 48 for sending and receiving signals, including information of the radiation X that is detected by the radiation detector 40, to and from the console 28. A shield plate of lead or the like should preferably be placed over the side surfaces of the cassette controller 46 and the transceiver 48 under the irradiated surface 36 of the casing 34, so as to protect the cassette controller 46 and the transceiver 48 against damage which would otherwise be caused if the cassette controllers 46 and the transceiver 48 were irradiated with radiation X.

Figure 3:
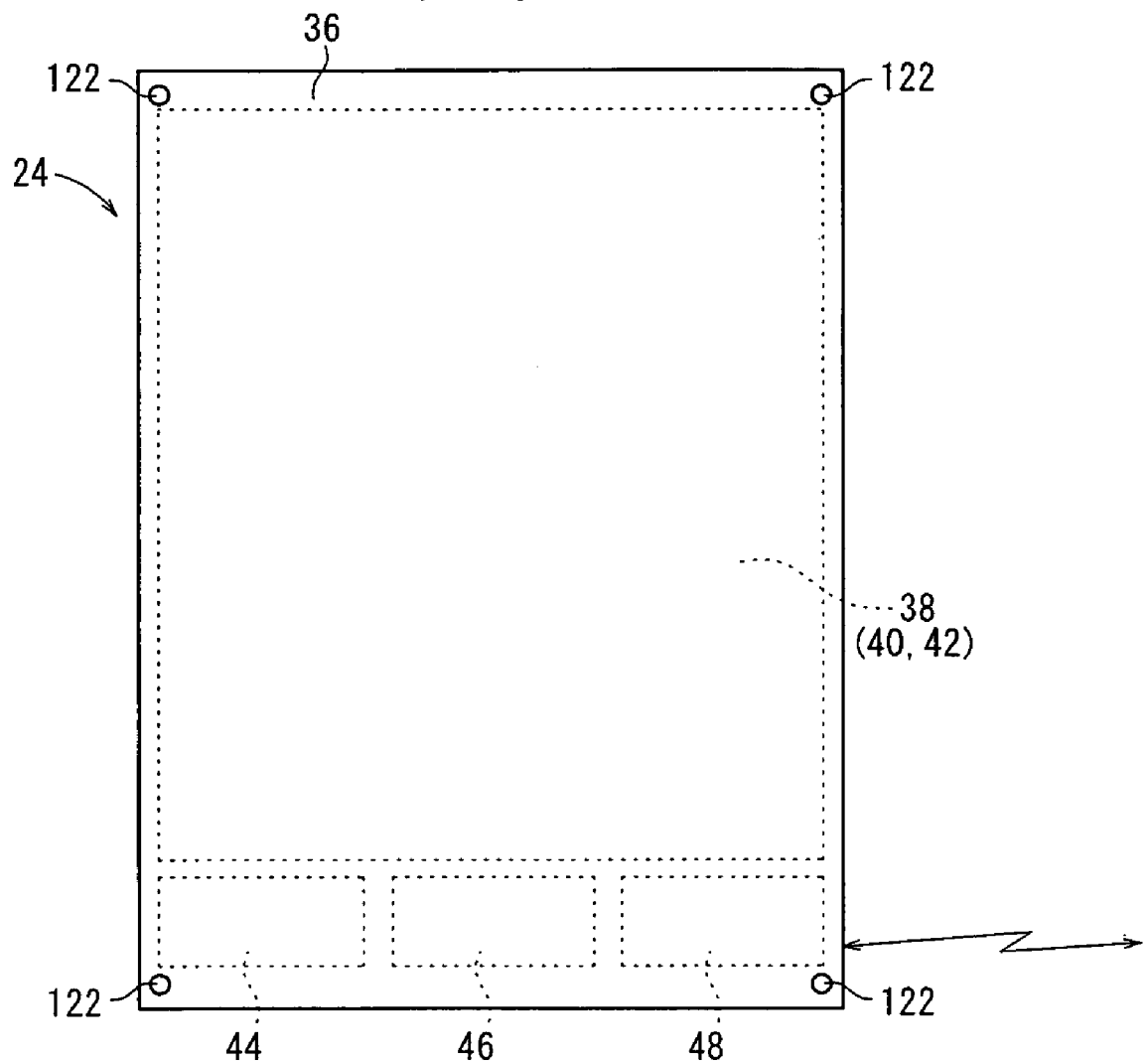
FIG. 3 is a plan view of the radiation detecting cassette shown in FIG. 2.
Figure 4:
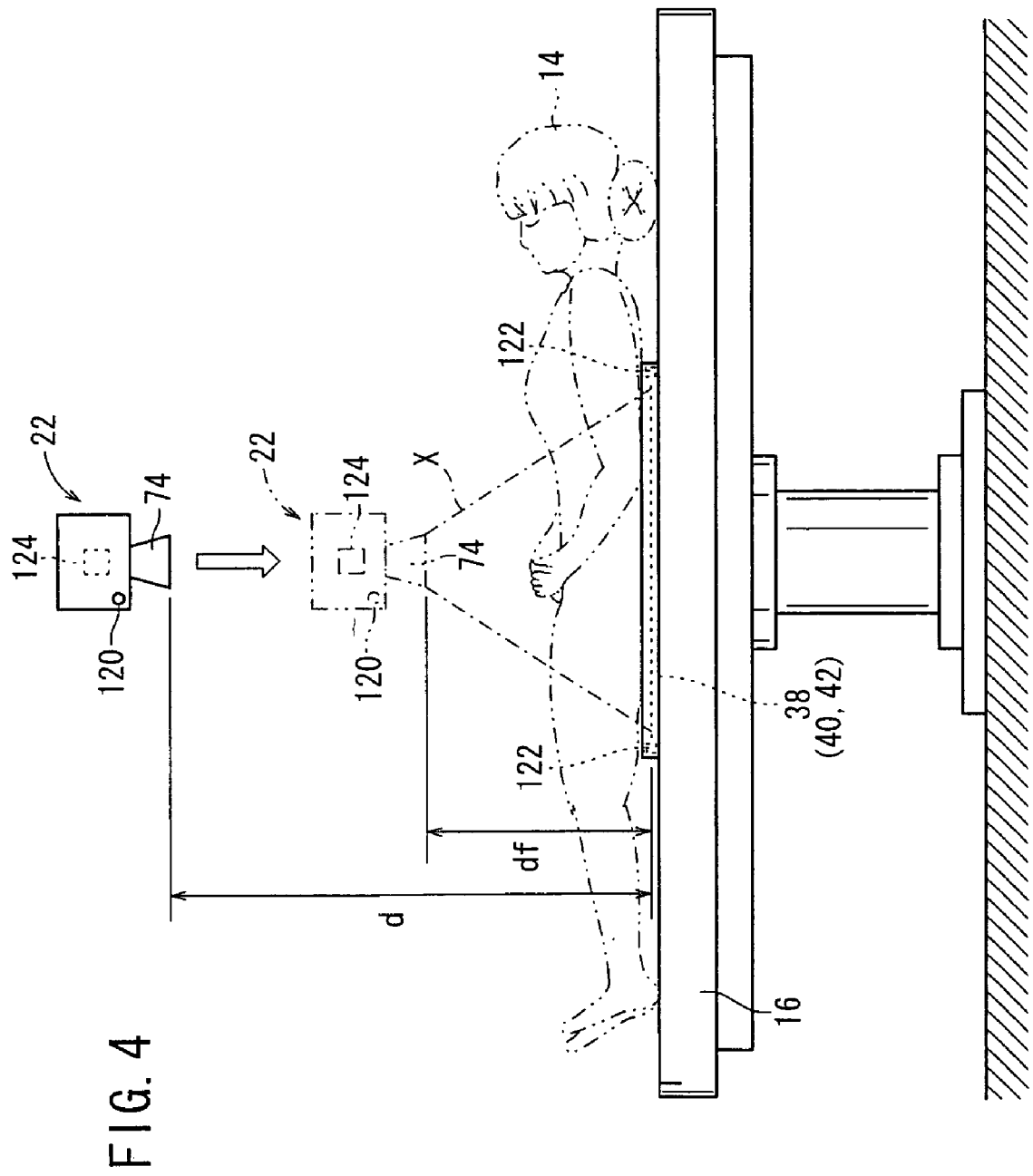
FIG. 4 is a side elevational view of an image capturing apparatus, a radiation detecting cassette, and a surgical table of the radiation image capturing system shown in FIG. 1.

FIG. 3 is a plan view of the radiation detecting cassette 24, and FIG. 4 is a side elevational view of the image capturing apparatus 22, the radiation detecting cassette 24, and the surgical table 16. As shown in FIGS. 2 through 4, the grid 38, the radiation detector 40, and the lead plate 42 are not disposed in the four corners of the casing 34, but signal generators 122 are disposed on the irradiated surface 36 respectively in the four corners of the casing 34. A signal detector 124 is disposed in the image capturing apparatus 22, correspondingly to the four signal generators 122. The signal detector 124 of the image capturing apparatus 22 is positioned to detect signals from the four signal generators 122 of the radiation detecting cassettes 24. Specifically, each of the signal generators 122 comprises a magnet or a magnetic generator, and the signal detector 124 comprises a three-axis magnetic field sensor for detecting a magnetic field that is generated continuously or intermittently by each of the magnets or the magnetic generators.

As shown in FIG. 4, it is assumed that the distance between the image capturing apparatus 22 and the radiation detecting cassettes 24, i.e., the distance between a radiation source 74 of the image capturing apparatus 22 and the radiation detector 40 of the radiation detecting cassettes 24 is represented by d. In the radiation image capturing system 10A, the distance d is adjusted into conformity with a predetermined distance (source-to-image distance, hereinafter also referred to as "SID") df from the radiation source 74 to the radiation detector 40 at the time a radiation image of the patient 14 is to be captured. Thereafter, the image capturing apparatus 22 applies the radiation X to the patient 14. The distance d may be adjusted when the image capturing apparatus 22 is moved to a desired position by controlling the universal arm 30 with a radiation source movement controller (moving unit) 132 (see FIG. 6), or when one of the surgeons 18 or the radiological technician manually moves the universal arm 30 and the image capturing apparatus 22.

Figure 5:
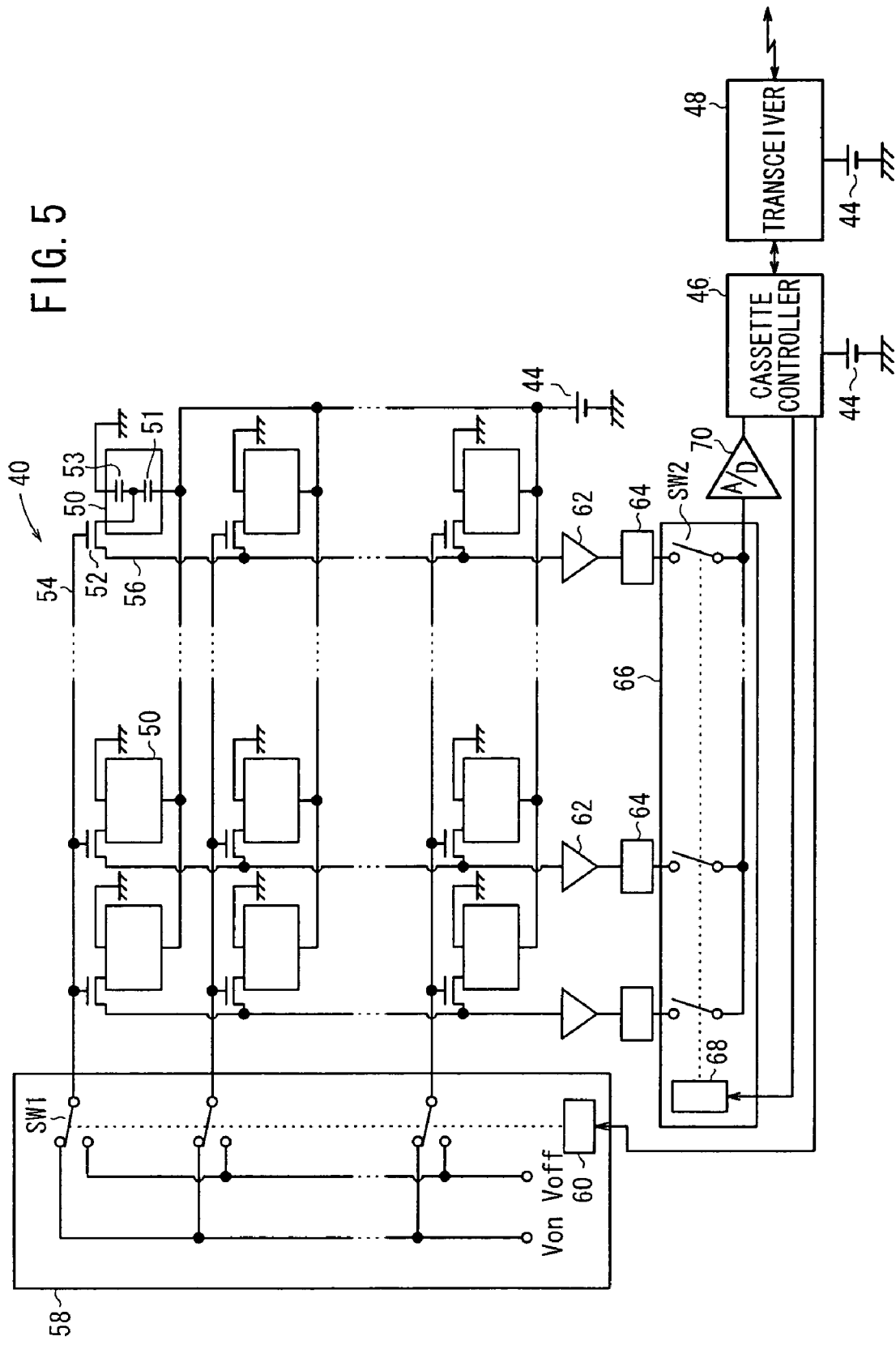
FIG. 5 is a block diagram of a circuit arrangement of a radiation detector in the radiation detecting cassette shown in FIG. 2.

FIG. 5 shows in block form a circuit arrangement of the radiation detector 40. As shown in FIG. 5, the radiation detector 40 comprises an array of thin-film transistors (TFTs) 52 arranged in rows and columns, a photoelectric conversion layer 51 made of a material such as amorphous selenium (a-Se) for generating electric charges upon detection of radiation X, the photoelectric conversion layer 51 being disposed over the array of TFTs 52, and an array of storage capacitors 53 connected to the photoelectric conversion layer 51. When the radiation X is applied to the radiation detector 40, the photoelectric conversion layer 51 generates electric charges, and the storage capacitors 53 store the generated electric charges. Then, the TFTs 52 are turned on along each row at a time, to read the electric charges from the storage capacitors 53 as an image signal. In FIG. 5, the photoelectric conversion layer 51 and one of the storage capacitors 53 are shown as making up a pixel 50, wherein the pixel 50 is connected to one of the TFTs 52. Details of the other pixels 50 are omitted from illustration. Since amorphous selenium tends to change its structure and lose its function at high temperatures, it needs to be used within a certain temperature range. Therefore, some means for cooling the radiation detector 40 should preferably be provided in the radiation detecting cassette 24.

The TFTs 52 which are connected to the respective pixels 50, are also connected to respective gate lines 54 extending in parallel to the rows, and to respective signal lines 56 extending in parallel to the columns. The gate lines 54 are connected to a line scanning driver 58, and the signal lines 56 are connected to a multiplexer 66 serving as a reading circuit. The gate lines 54 are supplied with control signals Von, Voff from the line scanning driver 58 for turning on and off the TFTs 52 along the rows. The line scanning driver 58 comprises a plurality of switches SW1 for switching between the gate lines 54, and an address decoder 60 for outputting a selection signal for selecting one of the switches SW1 at a time. The address decoder 60 is supplied with an address signal from the cassette controller 46.

The signal lines 56 are supplied with electric charges stored in the storage capacitors 53 of the pixels 50 through the TFTs 52 arranged in the columns. The electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of switches SW2 for successively switching between the signal lines 56 and an address decoder 68 for outputting a selection signal for selecting one of the switches SW2 at a time. The address decoder 68 is supplied with an address signal from the cassette controller 46. The multiplexer 66 has an output terminal connected to an A/D converter 70. A radiation image signal generated by the multiplexer 66 based on the electric charges from the sample and hold circuits 64 is converted by the A/D converter 70 into a digital image signal representing radiation image information, which is supplied to the cassette controller 46.

Figure 6:
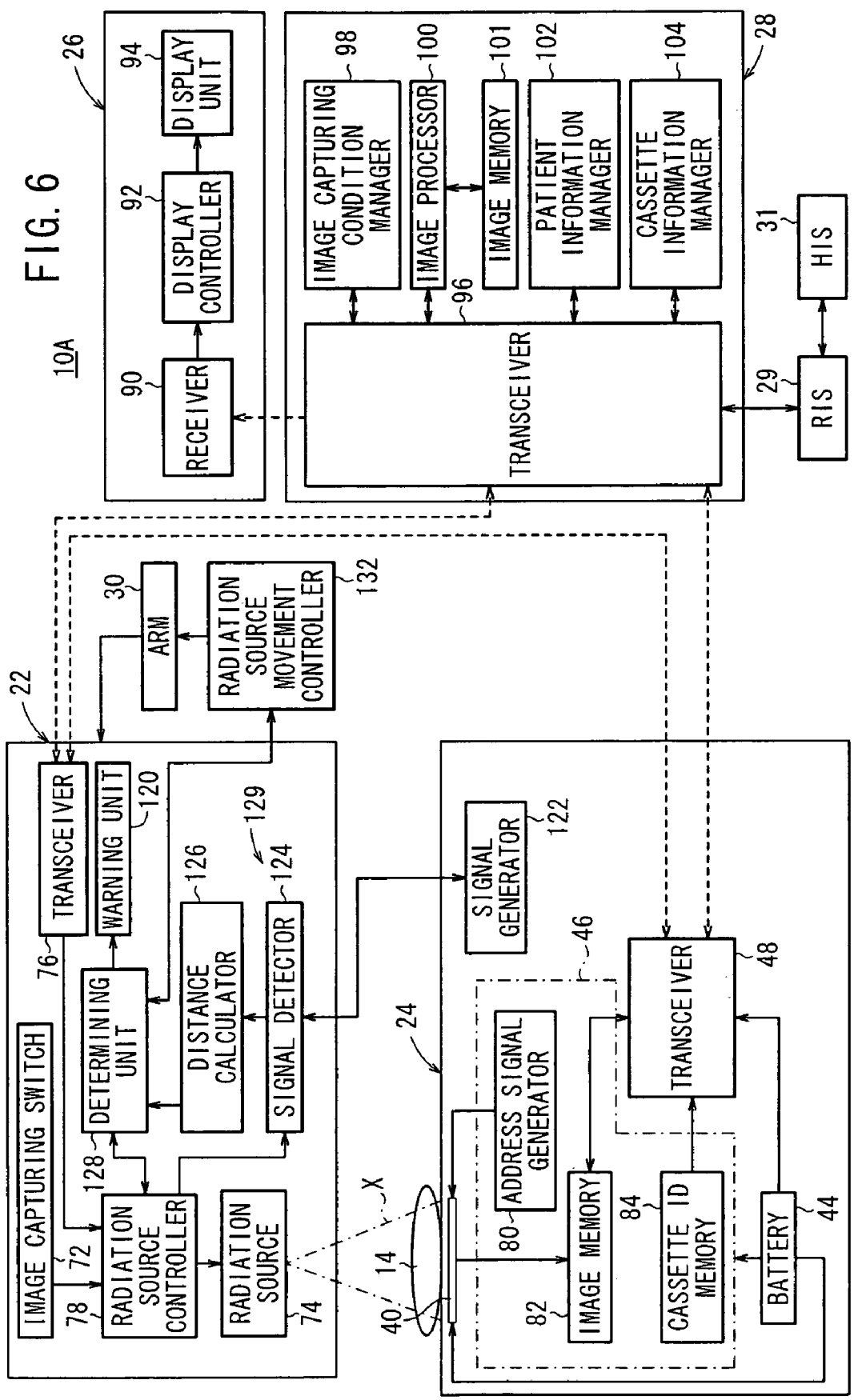
FIG. 6 is a block diagram of the radiation image capturing system shown in FIG. 1.

FIG. 6 shows in block form the radiation image capturing system 10A which comprises the image capturing apparatus 22, the radiation detecting cassette 24, the display device 26, and the console 28. The console 28 is connected to a radiology information system (RIS) 29, which generally manages radiation image information handled by the radiological department of the hospital along with other information. The RIS 29 is connected to a hospital information system (HIS) 31, which generally manages medical information in the hospital.

The image capturing apparatus 22 comprises an image capturing switch 72, a radiation source 74, a transceiver (second wireless communication unit) 76, a radiation source controller 78, a warning unit (warning means) 120, a signal detector 124, a distance calculator 126, and a determining unit (determining means) 128.

The transceiver 76 receives image capturing conditions from the console 28 by way of wireless communications, and transmits an image capturing completion signal, etc. to the console 28 by way of wireless communications. The transceiver 76 is also capable of performing wireless communications with the transceiver 48 of the radiation detecting cassette 24.

The radiation source controller 78 controls the radiation source 74, the signal detector 124, and the determining unit 128 based on an image capturing start signal supplied from the image capturing switch 72 and image capturing conditions supplied from the transceiver 76. The radiation source 74 outputs the radiation X under the control of the radiation source controller 78. The signal detector 124 detects signals transmitted from the signal generators 122 under the control of the radiation source controller 78.

The distance calculator 126 calculates the distance d (see FIG. 4) based on the signals from the signal generators 122 which have been detected by the signal detector 124. As described above, each of the signal generators 122 comprises a magnet or a magnetic generator, and the signal detector 124 comprises a three-axis magnetic field sensor for detecting a magnetic field that is generated continuously or intermittently by each of the magnets or the magnetic generators. Therefore, the distance calculator 126 calculates the three-dimensional positions and directions of the signal generators 122 with respect to the signal detector 124, based on the intensities of the magnetic fields detected by the magnetic sensor, and calculates the distance d from the three-dimensional positions and directions and the present position of the radiation source 74. Thus, the signal generators 122, the signal detector 124, and the distance calculator 126 jointly serve as a distance detecting unit 129 for detecting the distance d.

Under the control of the radiation source controller 78, the determining unit 128 determines whether the distance d calculated by the distance calculator 126 matches the SID df or not. If the distance d does not match the SID df, then the determining unit 128 outputs a control signal for equalizing the distance d with the SID df to the radiation source movement controller 132. The SID df is included in the image capturing conditions that are supplied from the console 28 via transceivers 96, 76 to the radiation source controller 78, as described above.

Based on the control signal from the determining unit 128, the radiation source movement controller 132 causes the universal arm 30 to move the image capturing apparatus 22 to a predetermined position depending on the SID df until the distance d matches the SID df. After having moved the image capturing apparatus 22, the radiation source movement controller 132 outputs, to the determining unit 128, a response signal indicative of the completion of the movement of the image capturing apparatus 22.

If the determining unit 128 judges that the distance d does not match the SID df, then the determining unit 128 outputs, to the warning unit 120, a warning signal indicating that the distance d does not match the SID df. If the determining unit 128 is supplied with the response signal from the radiation source movement controller 132, then the determining unit 128 stops outputting the warning signal to the warning unit 120.

At the time the warning unit 120 is supplied with the warning signal from the determining unit 128, the warning unit 120 energizes a light-emitting diode (LED), for example, to emit light, indicating that the distance d does not match the SID df, to the surgeons 18 or the radiological technician in the operating room 12.

The cassette controller 46 of the radiation detecting cassette 24 comprises an address signal generator 80, an image memory 82, and a cassette ID memory 84.

The address signal generator 80 supplies address signals to the address decoder 60 of the line scanning driver 58 and the address decoder 68 of the multiplexer 66 of the radiation detector 40. The image memory 82 stores radiation image information detected by the radiation detector 40. The cassette ID memory 84 stores cassette ID information for identifying the radiation detecting cassette 24.

The transceiver 48 receives a transmission request signal from the console 28 by way of wireless communications and transmits the cassette ID information stored in the cassette ID memory 84 and the radiation image information stored in the image memory 82 to the console 28 by way of wireless communications.

The display device 26 comprises a receiver 90 for receiving radiation image information from the console 28, a display controller 92 for controlling the display of the received radiation image information, and a display unit 94 for displaying radiation image information processed by the display controller 92.

The console 28 comprises the transceiver (third wireless communication unit) 96, an image capturing condition manager 98, an image processor (image processing unit) 100, an image memory 101, a patient information manager 102, and a cassette information manager 104.

The transceiver 96 transmits and receives, by way of wireless communications, necessary information including radiation image information to and from the image capturing apparatus 22, the radiation detecting cassette 24, and the display device 26. The image capturing condition manager 98 manages image capturing conditions required for the image capturing apparatus 22 to capture radiation images. The image processor 100 processes radiation image information transmitted from the radiation detecting cassette 24. The image memory 101 stores the radiation image information processed by the image processor 100. The patient information manager 102 manages patient information of the patient 14 whose images are to be captured. The cassette information manager 104 manages cassette ID information transmitted from the radiation detecting cassette 24.

The console 28 may be located outside of the operating room 12, assuming that the console 28 can transmit and receive signals to and from the image capturing apparatus 22, the radiation detecting cassette 24, and the display device 26 by way of wireless communications.

The image capturing conditions refer to condition for determining a tube voltage, a tube current, an irradiation time, etc., which are required to apply radiation X at an appropriate dose to an area of the patient 14 to be imaged. The image capturing conditions may include the SID df referred to above, an area of the patient 14 to be imaged, an image capturing method, etc., for example. The patient information refers to information used for identifying the patient 14, such as the patient's name, gender, patient ID number, etc. Ordering information for instructing the radiation image capturing system 10A to capture a radiation image, including the image capturing conditions and the patient information, can be set directly via the console 28, or can be supplied from an external source to the console 28 via the RIS 29.

The radiation image capturing system 10A according to the first embodiment is basically constructed as described above, and operations of the radiation image capturing system 10A will be described below.

The radiation image capturing system 10A is installed in the operating room 12 and used when a radiation image of the patient 14 is required by surgeons 18 who are performing an operation on the patient 14. Before a radiation image of the patient 14 is captured, patient information of the patient 14 to be imaged is registered in the patient information manager 102 of the console 28. If an area of the patient 14 to be imaged and an image capturing method are already known, such conditions are registered as image capturing conditions in the image capturing condition manager 98. After the above preparatory process is finished, the surgeons 18 perform the operation on the patient 14.

For capturing a radiation image of the patient 14 during the operation, one of the surgeons 18 or the radiological technician places the radiation detecting cassette 24 between the patient 14 and the surgical table 16, with the irradiated surface 36 facing the image capturing apparatus 22. Then, one of the surgeons 18 or the radiological technician moves the image capturing apparatus 22 to a position facing the radiation detecting cassette 24, and then turns on the image capturing switch 72 to capture a radiation image of the patient 14.

Figure 7:
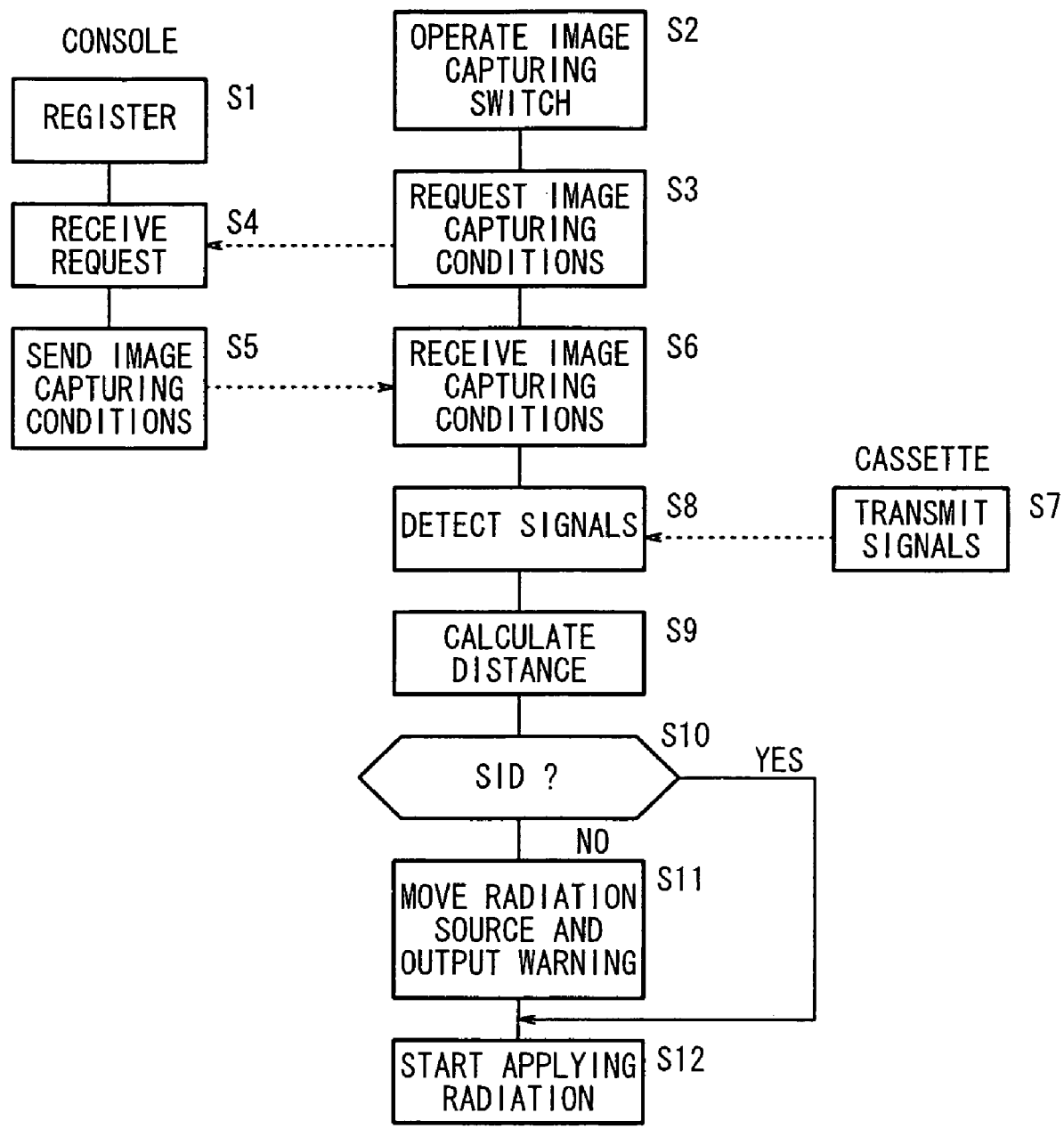
FIG. 7 is a flowchart of an operation sequence of the radiation image capturing system from the registration in a console to the application of a radiation.

FIG. 7 is a flowchart of an operation sequence of the radiation image capturing system 10A from the registration (step S1) and the operation of the image capturing switch 72 (step S2) to the application of the radiation X to the patient 14 (step S12).

The preparatory process is performed in step S1, and one of the surgeons 18 or the radiological technician turns on the image capturing switch 72 (see FIG. 6) in step S2. Then, the radiation source controller 78 of the image capturing apparatus 22 sends a request to the console 28 for sending the image capturing conditions via the transceivers 76, 96 in step S3.

The console 28 receives the request in step S4, and then sends the image capturing conditions for an area of the patient 14 to be imaged which are registered in the image capturing condition manager 98, to the image capturing apparatus 22 via the transceivers 96, 76 in step S5. The radiation source controller 78 receives the image capturing conditions in step S6, and controls the signal detector 124 to detect the signals transmitted from the signal generators 122, supplies, to the determining unit 128, the SID df included in the image capturing conditions, and controls the determining unit 128 to compare the supplied SID df with the distance d.

The signal generators 122 are continuously or intermittently transmitting signals in step S7. Under the control of the radiation source controller 78, the signal detector 124 detects the signals transmitted from the signal generators 122, and outputs the detected signals to the distance calculator 126 in step S8. The distance calculator 126 calculates the distance d based on the signals from the signal detector 124, and outputs the calculated distance d to the determining unit 128 in step S9. Under the control of the radiation source controller 78, the determining unit 128 determines whether the distance d matches the SID df or not in step S10.

If the determining unit 128 judges that the distance d does not match the SID df in step S10, then the determining unit 128 outputs, to the warning unit 120, a warning signal indicating that the distance d does not match the SID df, and also outputs, to the radiation source movement controller 132, a control signal to equalize the distance d with the SID df.

Based on the warning signal from the determining unit 128, the warning unit 120 indicates, to the surgeons 18 or the radiological technician through LED light emission or the like, that the distance d does not match the SID df. Based on the control signal from the determining unit 128, the radiation source movement controller 132 controls the universal arm 30 to move the image capturing apparatus 22 to a predetermined position of the radiation source 74 where the distance d matches the SID df. After having moved the image capturing apparatus 22, the radiation source movement controller 132 outputs, to the determining unit 128, a response signal indicative of the completion of the movement of the image capturing apparatus 22 in step S11.

Based on the response signal supplied to the determining unit 128, the determining unit 128 stops outputting the warning signal to the warning unit 120, and outputs the response signal to the radiation source controller 78. The warning unit 120 stops indicating, to the surgeons 18 or the radiological technician, that the distance d does not match the SID df. Further, based on the supplied response signal, the radiation source controller 78 controls the radiation source 74 to apply radiation X at a given dose to the patient 14 according to the image capturing conditions in step S12.

If the determining unit 128 judges that the distance d matches the SID df in step S10, then the determining unit 128 does not output the warning signal to the warning unit 120 or the control signal to the radiation source movement controller 132, but outputs, to the radiation source controller 78, a response signal indicating that the distance d matches the SID df. Based on the supplied response signal, the radiation source controller 78 executes the processing of step S12.

After step S12, radiation X that has passed through the patient 14 is applied to the grid 38, which removes scattered rays of the radiation X. Then, the radiation X is applied to the radiation detector 40, and converted into electric signals by the photoelectric conversion layer 51 of each of the pixels 50 of the radiation detector 40. The electric signals are stored as electric charges in the storage capacitors 53 (see FIG. 5). The stored electric charges, which represent radiation image information of the patient 14, are read from the storage capacitors 53 according to address signals which are supplied from the address signal generator 80 of the cassette controller 46 to the line scanning driver 58 and the multiplexer 66.

Specifically, in response to the address signal supplied from the address signal generator 80, the address decoder 60 of the line scanning driver 58 outputs a selection signal so as to select one of the switches SW1, which supplies the control signal Von to the gates of the TFTs 52 connected to the gate line 54 corresponding to the selected switch SW1. In response to the address signal supplied from the address signal generator 80, the address decoder 68 of the multiplexer 66 outputs a selection signal, which operates to successively turn on the switches SW2 so as to switch between the signal lines 56, for thereby reading the electric charges stored in the storage capacitors 53 of the pixels 50 connected to the selected gate line 54, through the signal lines 56.

The electric charges read from the storage capacitors 53 of the pixels 50, which are connected to the selected gate line 54, are amplified by respective amplifiers 62, sampled by the sample and hold circuits 64, and supplied to the multiplexer 66. Based on the supplied electric charges, the multiplexer 66 generates and supplies a radiation image signal to the A/D converter 70, which converts the radiation image signal into a digital signal. The digital signal, which represents the radiation image information, is stored in the image memory 82 of the cassette controller 46.

Similarly, the address decoder 60 of the line scanning driver 58 successively turns on the switches SW1 to switch between the gate lines 54 according to the address signal supplied from the address signal generator 80. The electric charges stored in the storage capacitors 53 of the pixels 50 connected to the successively selected gate lines 54 are read through the signal lines 56, and processed by the multiplexer 66 and the A/D converter 70 into digital signals, which are stored in the image memory 82 of the cassette controller 46.

The radiation image information represented by the digital signals stored in the image memory 82 is transmitted through the transceiver 48 to the console 28 by way of wireless communications.

The radiation image information transmitted to the console 28 is received by the transceiver 96, subjected to a predetermined image processing in the image processor 100, and then stored in the image memory 101 in association with the patient information of the patient 14 registered in the patient information manager 102.

The radiation image information processed by the image processor 100 is transmitted from the transceiver 96 to the display device 26. In the display device 26, the receiver 90 receives the radiation image information, and the display controller 92 controls the display unit 94 so as to display a radiation image based on the radiation image information. The surgeons 18 perform an operation on the patient 14 while visually confirming the radiation image displayed on the display unit 94.

In the radiation image capturing system 10A according to the first embodiment, the distance detecting unit 129 automatically detects the distance d between the radiation source 74 and the radiation detector 40 of the radiation detecting cassette 24, and the determining unit 128 automatically determines whether the distance d matches the SID df or not. Accordingly, before a radiation image of the patient 14 is captured, it is possible to adjust the distance d to the SID df easily and highly accurately for generating radiation image information of high accuracy.

Even if one of the surgeons 18 or the radiological technician manually operates the universal arm 30 to adjust the distance d before a radiation image of the patient 14 is captured, the distance d is automatically detected and automatically checked against the SID df. Consequently, the burden on the surgeons 18 and the radiological technician is greatly reduced for efficiently capturing radiation images.

If the determining unit 128 judges that the distance d does not match the SID df, then the radiation source movement controller 132 can automatically control the universal arm 30 to move the image capturing apparatus 22 until the distance d matches the SID df. In other words, the distance d is automatically detected and automatically checked against the SID df, and the distance d is automatically adjusted to mach the SID df. Consequently, the burden on the surgeons 18 and the radiological technician is further reduced, and the distance d is adjusted to the SID df reliably and highly accurately for generating radiation image information of high accuracy.

If the determining unit 128 judges that the distance d does not match the SID df, then the warning unit 120 indicates that the distance d does not match the SID df, to the surgeons 18 or the radiological technician present in the operating room 12. At this time, one of the surgeons 18 or the radiological technician can manually operate the universal arm 30 to adjust the distance d to the SID df, without allowing the radiation source movement controller 132 to operate. Therefore, the surgeon 18 and the radiological technician can adjust the distance d efficiently without suffering an increase in the burden thereon.

Furthermore, signals are transmitted and received by way of the UWB wireless communications between the radiation detecting cassette 24 and the console 28, between the radiation detecting cassette 24 and the image capturing apparatus 22, between the image capturing apparatus 22 and the console 28, and between the console 28 and the display device 26. In other words, since cables for transmitting and receiving signals are not connected between the image capturing apparatus 22, the radiation detecting cassette 24, the display device 26, and the console 28, such cables are not placed on the floor of the operating room 12 where they would become obstacles to the operation performed by the surgeons 18, the radiological technician, or to other staff members present in the operating room 12. The surgeons 18, the radiological technician, and the other staff members in the operating room 12 can thus work more efficiently. The UWB wireless communications make it possible to reduce power consumption, increase fading resistance, and increase communication rates, compared with other wireless communications according to the related art.

The distance detecting unit 129 comprises the signal generators 122 on the radiation detecting cassette 24 and the signal detector 124 and the distance calculator 126 in the image capturing apparatus 22. The signal detector 124 detects signals transmitted from the signal generators 122, and the distance calculator 126 calculates the distance d based on the detected signals. As described above, since each of the signal generators 122 comprises a magnet or a magnetic generator, and the signal detector 124 comprises a three-axis magnetic field sensor for detecting a magnetic field that is generated continuously or intermittently by each of the magnets or the magnetic generators, the distance calculator 126 accurately calculates the distance d from the magnetic fields detected by the magnetic field sensor.

In the radiation image capturing system 10A according to the first embodiment, the signal generators 122 are disposed in the four corners of the casing 34 on the irradiated surface 36 of each of the radiation detecting cassettes 24, and the distance detecting unit 129 detects the distance d based on the magnetic fields generated by the signal generators 122. Insofar as the distance calculator 126 calculates the distance d based on the three-dimensional positions and directions of the radiation detector 40 and the radiation source 74, then each of the radiation detecting cassettes 24 may preferably have at least three signal generators 122.

Furthermore, the number of signal generators 122 on each of the radiation detecting cassettes 24 is not limited to three or four, but may be varied depending on how the distance detecting unit 129 detects the distance d.

Specifically, if the distance detecting unit 129 detects the distance d using an ultrasonic wave, then the number of signal generators 122 may be at least one, e.g., one ultrasonic wave reflector is disposed in any one of the four corners of the casing 34 on the irradiated surface 36 of the radiation detecting cassette 24, and the signal detector 124 comprises an ultrasonic wave transceiver for emitting an ultrasonic wave toward the ultrasonic wave reflector and receiving the ultrasonic wave reflected from the ultrasonic wave reflector. The distance calculator 126 calculates the distance d based on the period of time consumed after the ultrasonic wave transceiver emits the ultrasonic wave and until it receives the reflected ultrasonic wave.

If the distance detecting unit 129 detects the distance d using UWB wireless transmissions, then the number of signal generators 122 may also be at least one, e.g., one wireless signal transmitter is disposed in any one of the four corners of the casing 34 on the irradiated surface 36 of the radiation detecting cassette 24, and the signal detector 124 comprises a wireless signal receiver for receiving UWB wireless signal sent from the wireless signal transmitter. The distance calculator 126 calculates the distance d based on the period of time consumed after the wireless signal transmitter transmits the UWB wireless signal and until the wireless signal receiver receives the UWB wireless signal. In this case, for example, time synchronization needs to be kept in advance between the signal generator 122 and the signal detector 124, using an atomic radio clock.

Alternatively, if the distance detecting unit 129 detects the distance d using UWB wireless transmissions, then the number of signal generators 122 may also be at least one, e.g., one wireless signal reflector is disposed in any one of the four corners of the casing 34 on the irradiated surface 36 of the radiation detecting cassette 24, and the signal detector 124 comprises a wireless signal transceiver for emitting a radio wave toward the wireless signal reflector and receiving a radio wave reflected from the wireless signal reflector. The distance calculator 126 calculates the distance d based on the period of time consumed after the wireless signal transceiver emits the radio wave and until it receives the reflected radio wave.

If the signal generator 122 is a composite sensor comprising a geomagnetic sensor, a gravitational sensor, and a three-dimensional gyroscope, then the gravitational sensor outputs the gravitational acceleration of the radiation detecting cassette 24, the geomagnetic sensor outputs the direction of geomagnetism, and the three-dimensional gyroscope outputs the attitude of the radiation detecting cassette 24. The signal detector 124 receives (detects) detected signals from the signal generator (composite sensor) 122, which represent the gravitational acceleration, the direction of geomagnetism, and the attitude, by way of wireless communications, and the distance calculator 126 calculates the distance d based on the detected signals.

As the distance detecting unit 129 can accurately detect the distance d using the magnetic, ultrasonic, wireless, or composite sensor, the determining unit 128 can accurately compare the distance d with the SID df.

If the distance detecting unit 129 detects the distance d using wireless signals, then the distance detecting unit 129 should preferably comprise a UWB pulse radar and use pulsed radio waves with no carriers for detecting the distance d. The UWB wireless communications make it possible to reduce power consumption, increase fading resistance, increase communication rates, and increase positional accuracy.

In the radiation image capturing system 10A according to the first embodiment, the signal generators 122 are mounted on the radiation detecting cassette 24, and the warning unit 120, the signal detector 124, the distance calculator 126, and the determining unit 128 are disposed in the image capturing apparatus 22. However, insofar as the distance d can be adjusted to the SID df, the signal generators 122 may be disposed in the image capturing apparatus 22, and the warning unit 120, the signal detector 124, the distance calculator 126, and the determining unit 128 may be disposed in the radiation detecting cassette 24.

In the radiation image capturing system 10A according to the first embodiment, the radiation source movement controller 132 controls the universal arm 30 to move the image capturing apparatus 22 to equalize the distance d with the SID df based on the control signal from the determining unit 128. However, for equalizing the distance d with the SID df, a moving unit, not shown, may be actuated to move the radiation detecting cassette 24, or such a moving unit may be actuated to move the radiation detecting cassette 24 at the same time that the radiation source movement controller 132 controls the universal arm 30 to move the image capturing apparatus 22.

The radiation image capturing system 10A according to the first embodiment captures a radiation image of the patient 14 when one of the surgeons 18 or the radiological technician turns on the image capturing switch 72. However, the radiation image capturing system 10A may also be configured to capture a radiation image of the patient 14 when one of the surgeons 18 or the radiological technician operates the console 28.

In the above illustrated embodiment, the warning unit 120 indicates that the distance d does not match the SID df, to the surgeons 18 or the radiological technician. However, the determining unit 128 may send a warning signal to the console 28 via the radiation source controller 78 and the transceivers 76, 96, and the console 28 may control the display controller 92 via the transceiver 96 and the receiver 90 to display a warning on the display unit 94 based on the warning signal. In this case, as the determining unit 128 sends a warning signal to the console 28, the console 28 can easily recognize whether the distance d matches the SID df or not.

In the radiation image capturing system 10A according to the first embodiment, the radiation detector 40, which is housed in the radiation detecting cassette 24, directly converts the dose of the applied radiation X into an electric signal via the photoelectric conversion layer 51. However, the radiation image capturing system 10A may employ a radiation detector including a scintillator for converting the applied radiation X into visible light together with a solid-state detecting device made up of amorphous silicon (a-Si) or the like for converting the visible light into an electric signal (see Japanese Patent No. 3494683).

Alternatively, the radiation image capturing system 10A may employ a light-conversion radiation detector for acquiring radiation image information. The light-conversion radiation detector operates as follows: When a radiation is applied to a matrix of solid-state detecting devices, the solid-state detecting devices store an electrostatic latent image therein depending on the dose of the applied radiation. For reading the stored electrostatic latent image, reading light is applied to the solid-state detecting devices, thereby causing the solid-state detecting devices to generate an electric current representing the radiation image information. When erasing light is applied to the radiation detector, radiation image information representing a residual electrostatic latent image is erased from the radiation detector, which can thus be reused (see Japanese Laid-Open Patent Publication No. 2000-105297).

A radiation image capturing system 10B according to a second embodiment of the present invention will be described below with reference to FIGS. 8 through 10. Those parts of the radiation image capturing system 10B which are identical to those of the radiation image capturing system 10A according to the first embodiment (see FIGS. 1 through 7) are denoted by identical reference characters, and will not be described in detail below.

The radiation image capturing system 10B according to the second embodiment is different from the radiation image capturing system 10A according to the first embodiment in that the surgical table 16 has the signal detector 124 and a transceiver 134, the image capturing apparatus 22 has the image capturing switch 72, the radiation source 74, the transceiver 76, the radiation source controller 78, the warning unit 120, the distance calculator 126, and the determining unit 128, and signals are sent and received between the transceiver 76 and the transceiver 134 by way of UWB wireless communications.

Figure 8:
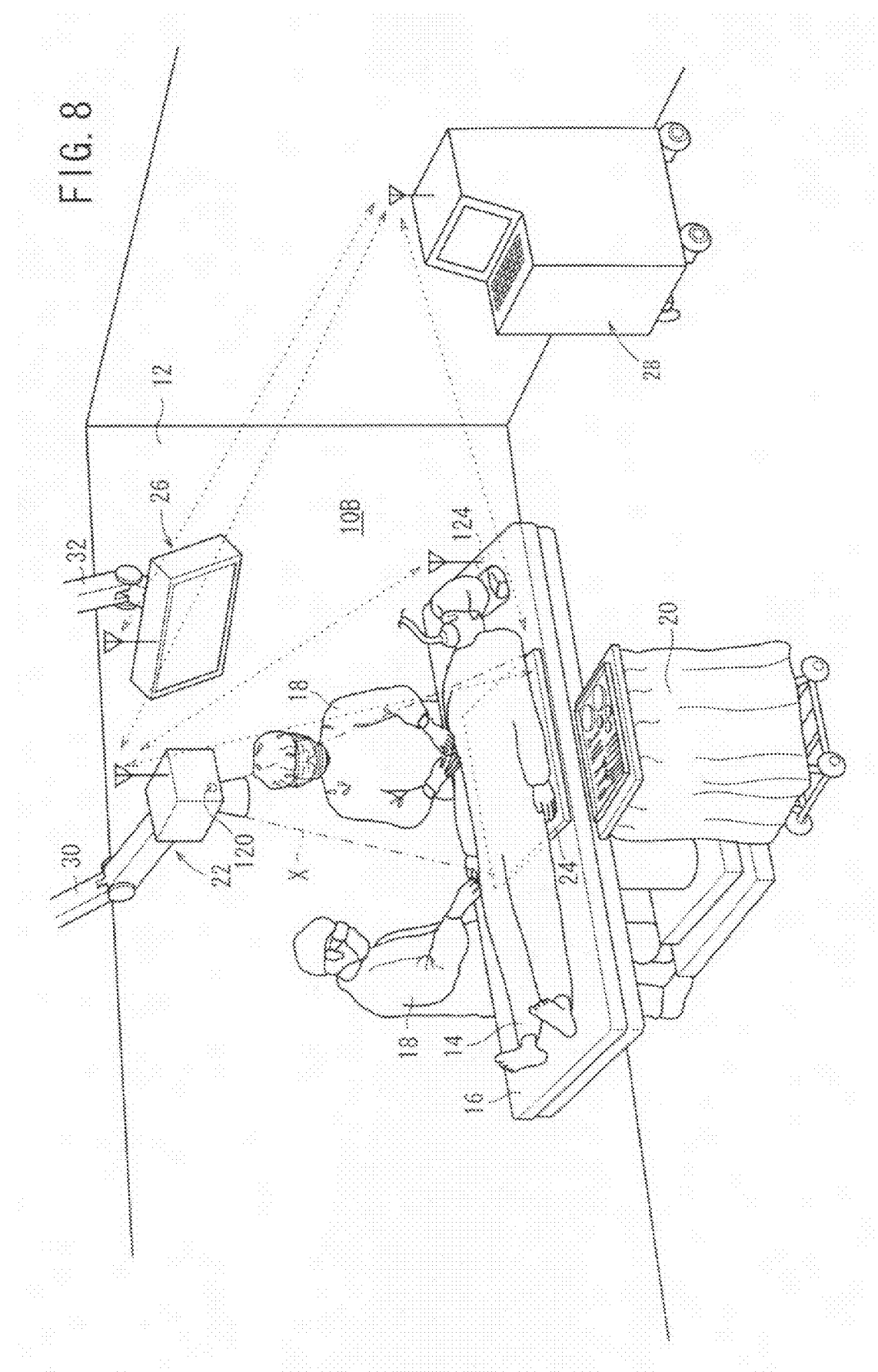
FIG. 8 is a perspective view of an operating room incorporating a radiation image capturing system according to a second embodiment of the present invention.
Figure 9:
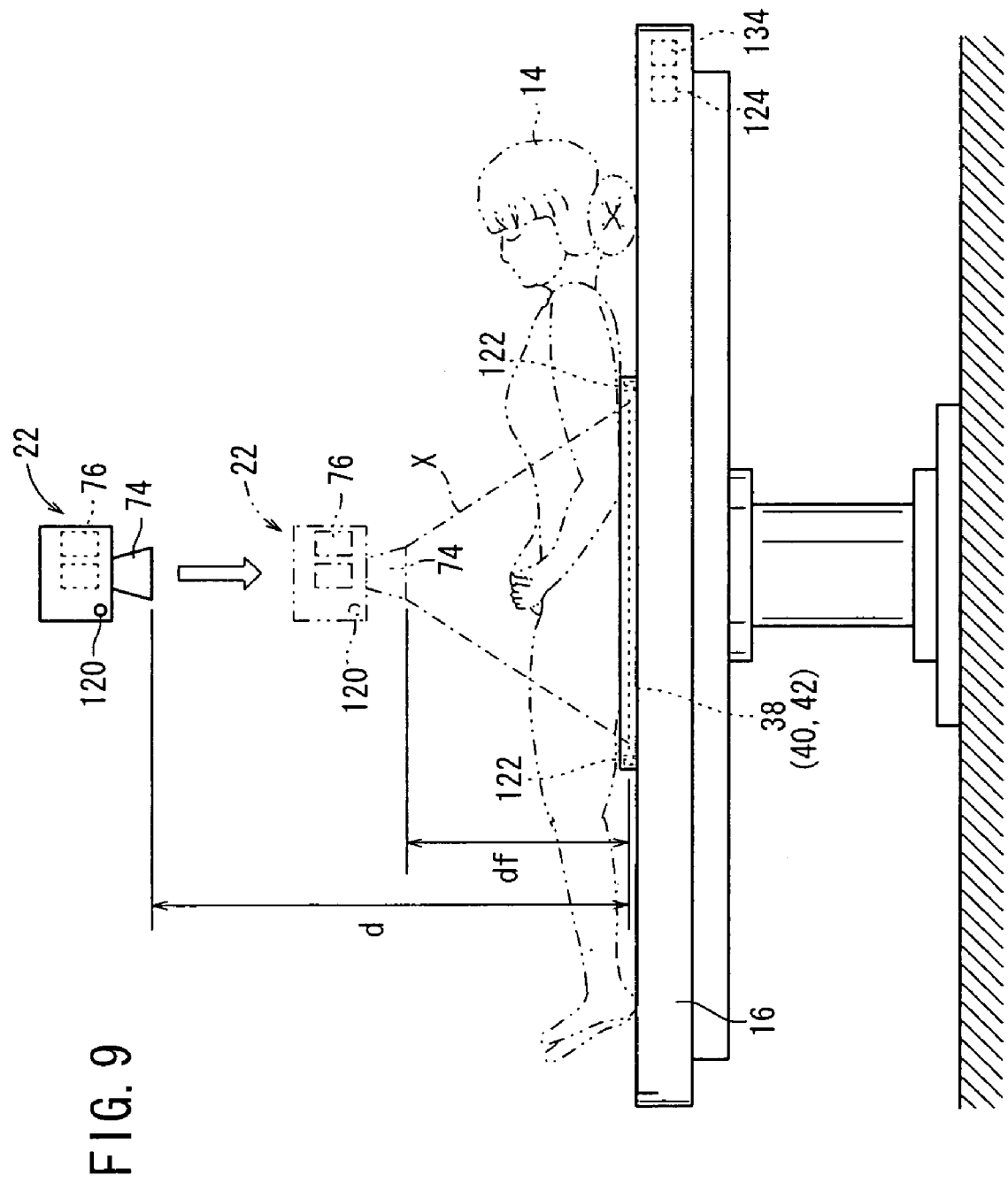
FIG. 9 is a side elevational view of an image capturing apparatus, a radiation detecting cassette, and a surgical table of the radiation image capturing system shown in FIG. 8.
Figure 10:
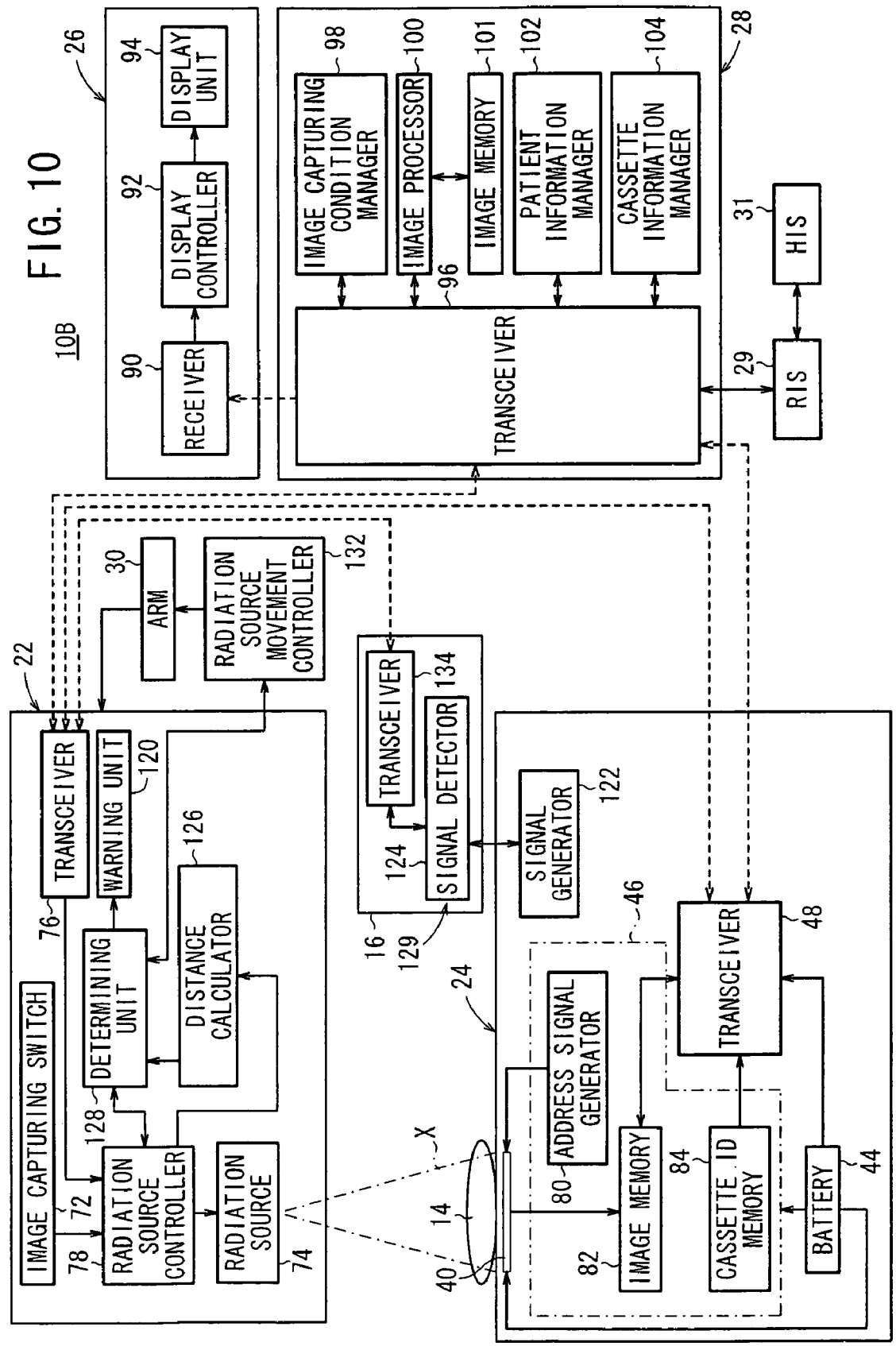
FIG. 10 is a block diagram of the radiation image capturing system shown in FIG. 8.

As shown in FIGS. 8 through 10, the signal detector 124 and the transceiver 134 are disposed in the surgical table 16. The signal detector 124 detects signals from the signal generators 122 under the control of the radiation source controller 78 via the transceivers 76, 134. The transceiver 134 outputs the signals detected by the signal detector 124, to the distance calculator 126 via the transceiver 76 and the radiation source controller 78.

Based on the signals from the signal generators 122 which have been detected by the signal detector 124, the distance calculator 126 calculates the position and direction of the radiation detector 40 with respect to the signal detector 124. If each of the signal generators 122 comprises a magnet or a magnetic generator, and the signal detector 124 comprises a three-axis magnetic field sensor for detecting a magnetic field that is generated continuously or intermittently by each of the magnets or the magnetic generators, then the distance calculator 126 calculates the three-dimensional positions and directions of the signal generators 122 with respect to the signal detector 124 based on the intensities of the magnetic fields detected by the magnetic sensor, and calculates the position and direction of the radiation detector 40 with respect to the signal detector 124 based on the calculated three-dimensional positions and directions.

Then, the distance calculator 126 calculates the distance d between the radiation source 74 and the radiation detector 40 based on the present position of the radiation source 74 which has been detected by a three-dimensional positional sensor, not shown, disposed in the image capturing apparatus 22, the present position of the signal detector 124, and the position and direction of the radiation detector 40 with respect to the signal detector 124. If the surgical table 16 is positionally fixed, then since the present position of the signal detector 124 is already known, the distance calculator 126 can easily calculate the distance d.

In the radiation image capturing system 10B according to the second embodiment, the signal detector 124 disposed in the surgical table 16 outputs the signals from the signal generators 122, to the distance calculator 126 via the transceivers 134, 76 and the radiation source controller 78, and signals are sent and received between the transceiver 76 and the transceiver 134 by way of UWB wireless communications. Accordingly, the radiation image capturing system 10B according to the second embodiment offers the same advantages as the radiation image capturing system 10A according to the first embodiment.

Figure 11:
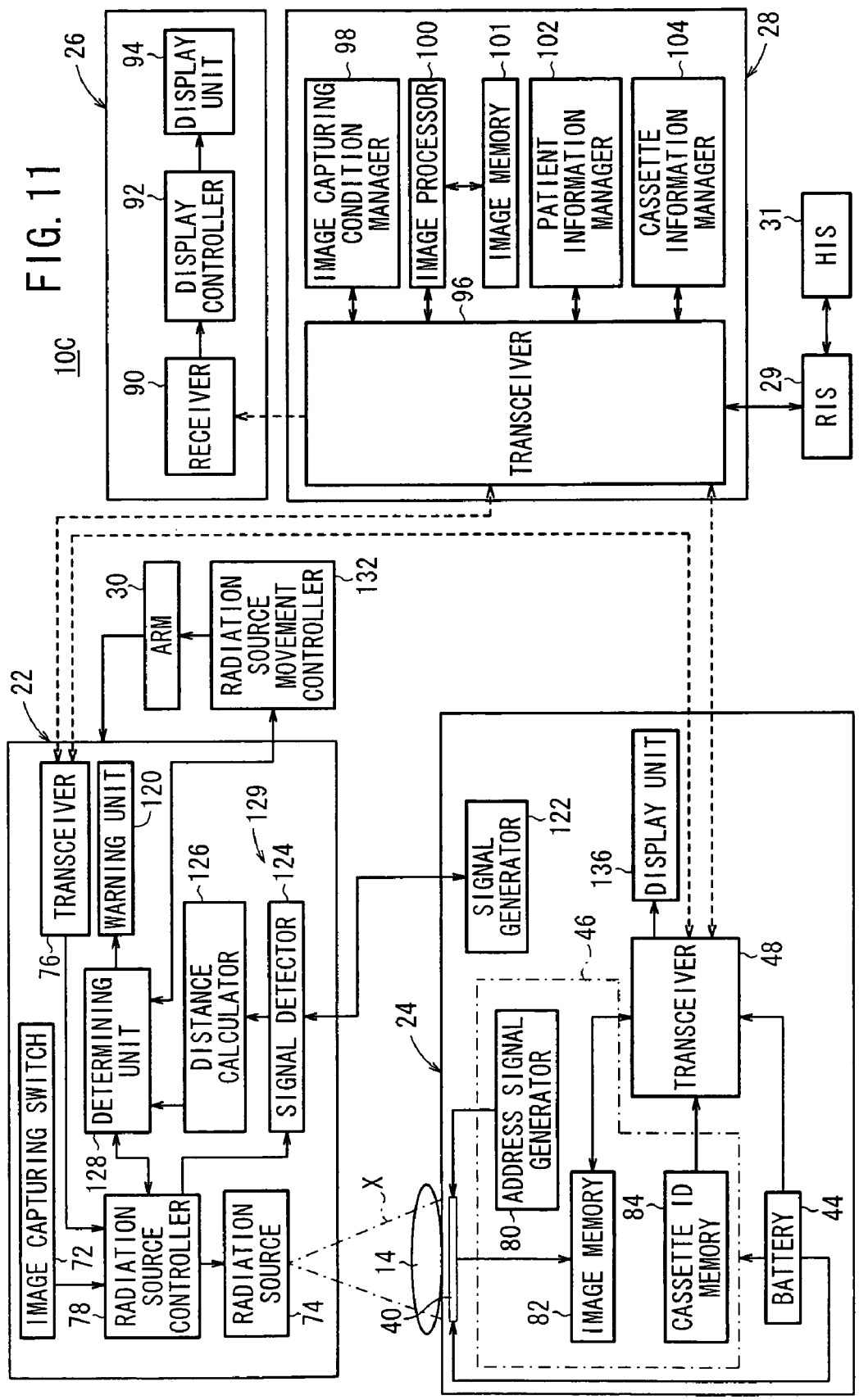
FIG. 11 is a block diagram of a radiation image capturing system according to a third embodiment of the present invention.

A radiation image capturing system 10C according to a third embodiment of the present invention will be described below with reference to FIGS. 11 through 13.

The radiation image capturing system 10C according to the third embodiment is different from the radiation image capturing systems 10A, 10B according to the first and second embodiments (see FIGS. 1 through 10) in that the radiation detecting cassette 24 has a display unit (display means) 136 for indicating its own position.

The radiation image capturing system 10C is available in two types. One of the types, which is shown in FIG. 11, is similar to the radiation image capturing system 10A according to the first embodiment except for the display unit 136 incorporated in the radiation detecting cassette 24.

Figure 12:
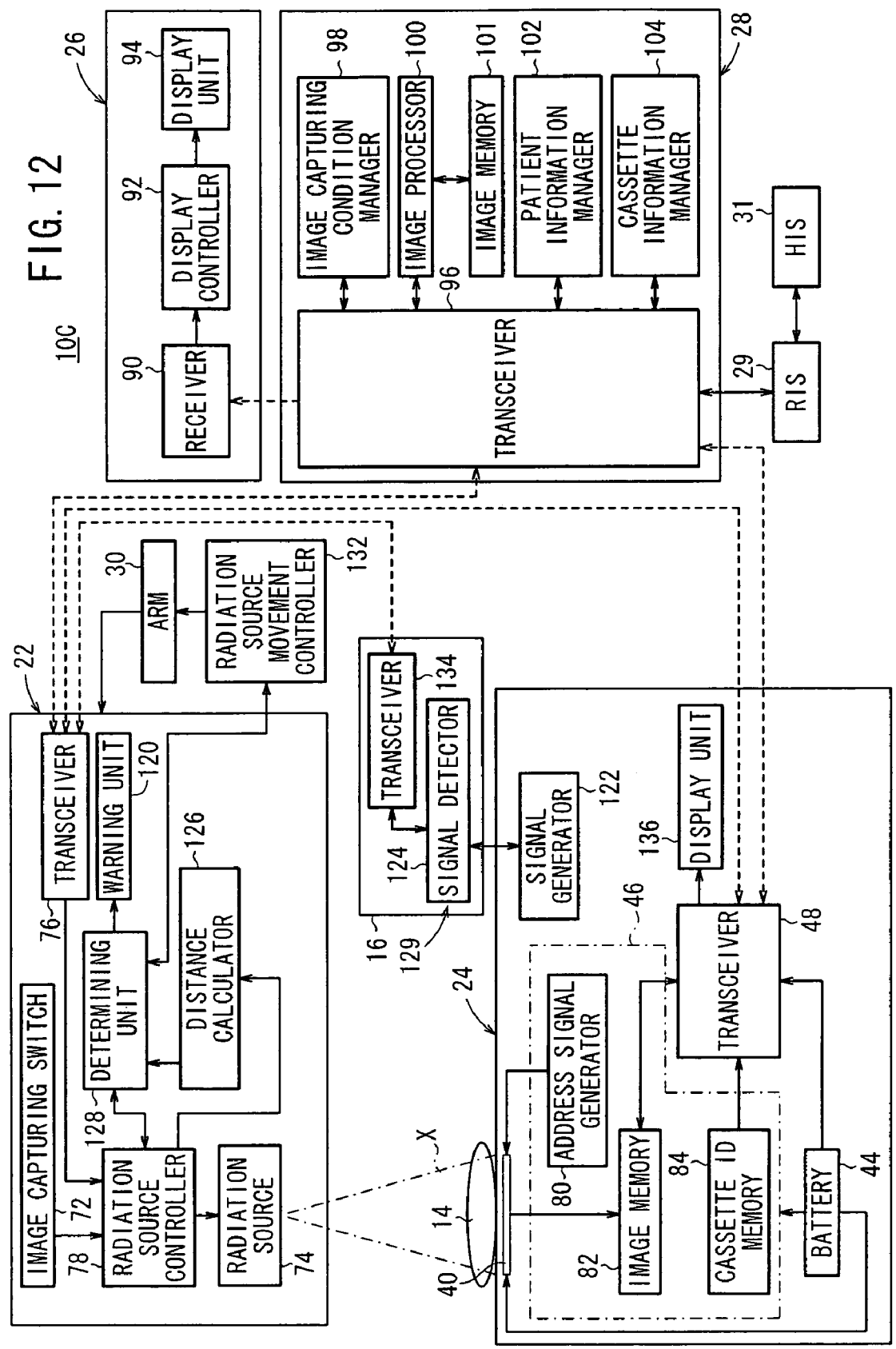
FIG. 12 is another block diagram of the radiation image capturing system according to the third embodiment of the present invention.

The other type, which is shown in FIG. 12, is similar to the radiation image capturing system 10B according to the second embodiment except for the display unit 136 incorporated in the radiation detecting cassette 24.

Figure 13:
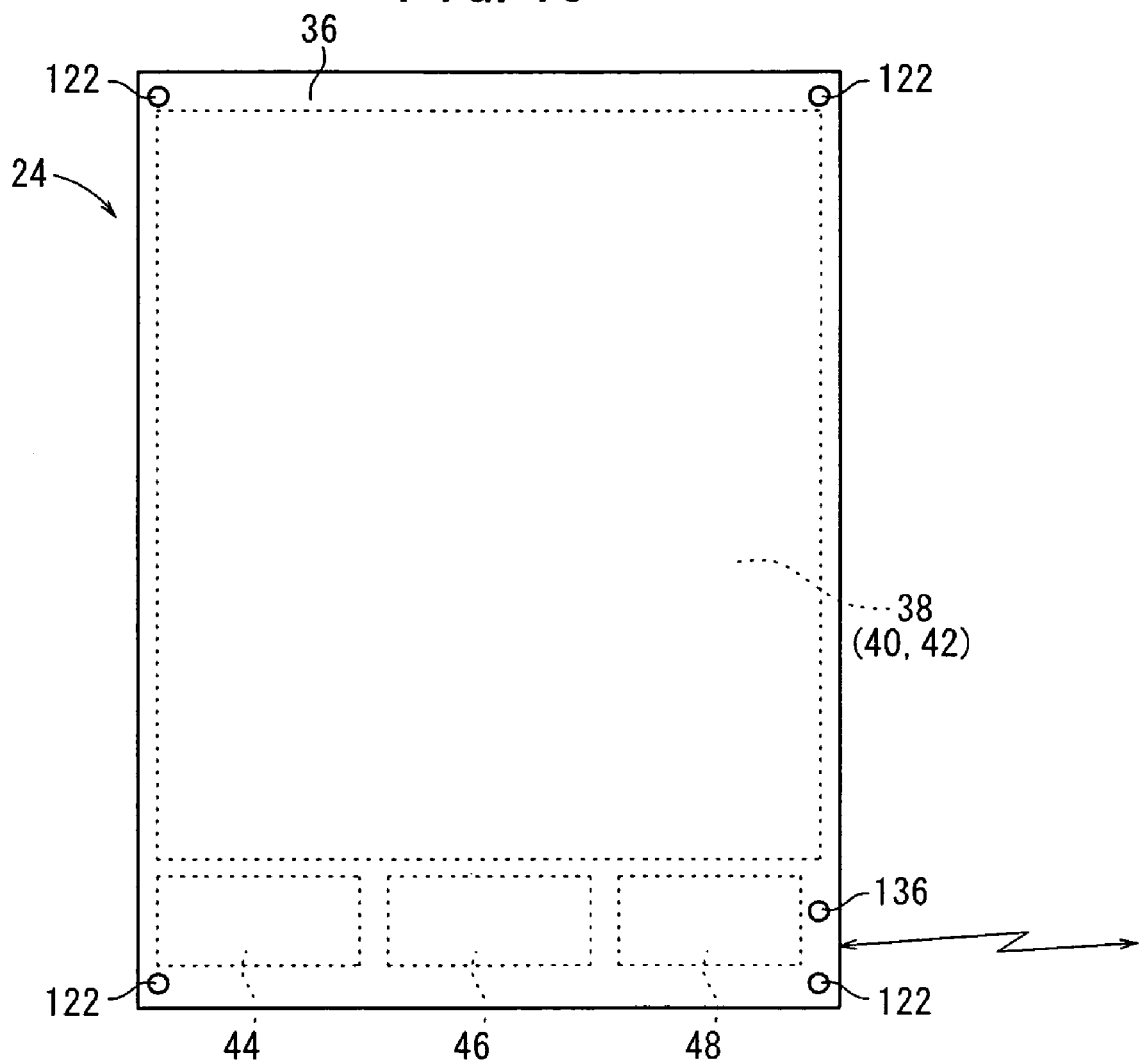
FIG. 13 is a plan view of a radiation detecting cassette used in the radiation image capturing system shown in FIGS. 11 and 12.

As shown in FIG. 13, the display unit 136 comprises an LED, for example, disposed on the irradiated surface 36 in any one of the four corners of the casing 34 of the radiation detecting cassette 24. Based on an indication instruction signal sent from the transceiver 96 of the console 28 (see FIGS. 11 and 12) to the transceiver 48 by way of wireless communications, or sent from the transceiver 96 via the transceiver 76 to the transceiver 48 by way of wireless communications, the LED is energized to emit light, thereby indicating the position of the radiation detecting cassette 24, to the surgeons 18 or the radiological technician in the operating room 12.

Since the display unit 136 indicates the present position of the radiation detecting cassette 24 to the surgeons 18 or the radiological technician, based on the indication instruction signal sent from the console 28 to the radiation detecting cassette 24, if the indication instruction signal is a signal for indicating a cassette that can be used at present, then the surgeons 18 or the radiological technician can easily identify a radiation detecting cassette 24 whose display unit 136 is currently indicating its position, as a cassette that can be used at present, and can place the radiation detecting cassette 24 between the patient 14 and the surgical table 16 for performing a surgical operation.

A radiation image capturing system 10D according to a fourth embodiment of the present invention will be described below with reference to FIGS. 14 and 15.

The radiation image capturing system 10D according to the fourth embodiment is different from the radiation image capturing systems 10A, 10B, 10C according to the first, second, and third embodiments (see FIGS. 1 through 13) in that a charging device 138 for charging the battery 44 of the radiation detecting cassette 24 is disposed near the console 28, and signals are sent and received between a transceiver 150 of the charging device 138 and the transceiver 96 of the console 28 by way of UWB wireless communications.

Figure 14:
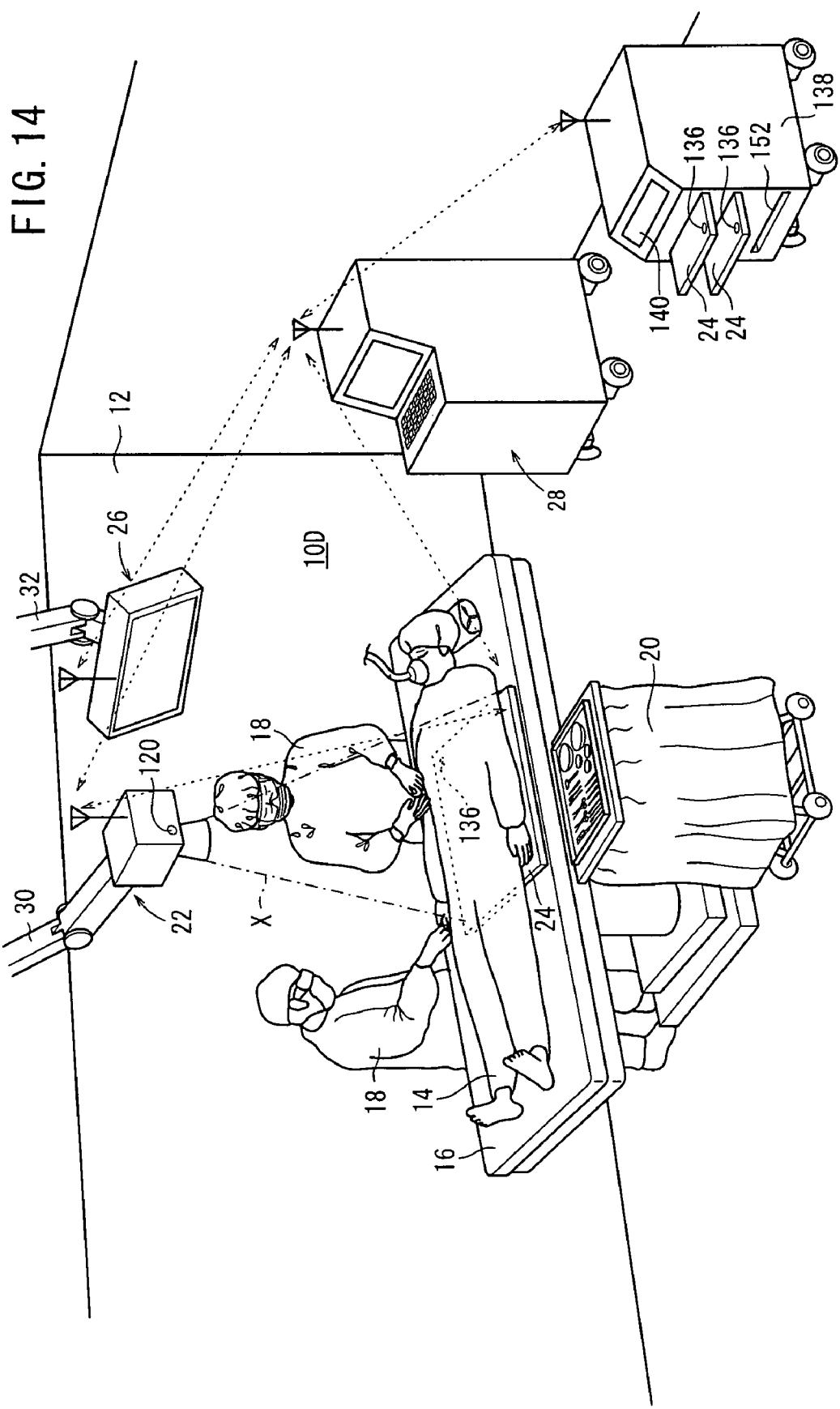
FIG. 14 is a perspective view of an operating room incorporating a radiation image capturing system according to a fourth embodiment of the present invention.

As shown in FIG. 14, the charging device 138 has a plurality of slots 152 defined in a front side thereof for loading radiation detecting cassettes 24 respectively therein. The charging device 138 also has a display unit 140 on an upper portion of the front side for indicating that the batteries 44 of the radiation detecting cassettes 24 loaded in the charging device 138 are being charged.

Figure 15:
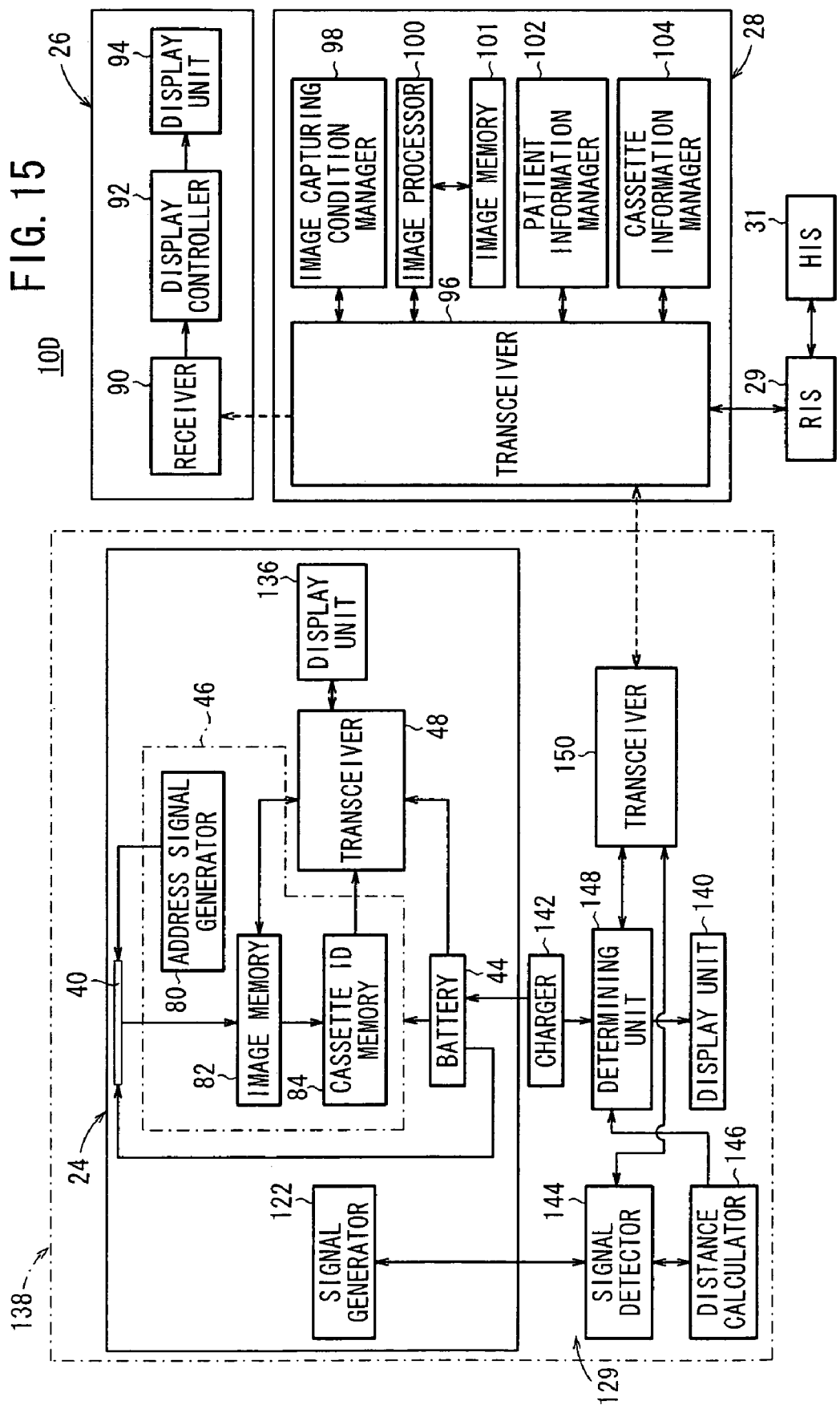
FIG. 15 is a block diagram of the radiation image capturing system shown in FIG. 14.

As shown in FIG. 15, the charging device 138 includes the transceiver 150, the display unit 140, a signal detector 144, a distance calculator 146, and a determining unit 148 which have essentially the same functions as the signal detector 124, the distance calculator 126, and the determining unit 128 (see FIGS. 6, 10 through 12), respectively, and a charger 142 for charging the battery 44. The signal generators 122 of each of the radiation detecting cassettes 24 loaded in the charging device 138, and the signal detector 144 and the distance calculator 146 of the charging device 138 jointly serve as a distance detecting unit 129. In FIG. 15, the patient 14, the image capturing apparatus 22, the universal arm 30, and the radiation source movement controller 132 are omitted from illustration for illustrative purposes.

When a radiation detecting cassette 24 is loaded into the charging device 138 through one of the slots 152, the charger 142 starts charging the battery 44 of the loaded radiation detecting cassette 24, and outputs a charging start signal to the display unit 140 through the determining unit 148. Based on the supplied charging start signal, the display unit 140 indicates that the battery 44 of the loaded radiation detecting cassette 24 is being charged.

The console 28 sends a control signal for confirming whether the radiation detecting cassette 24 is being loaded in the charging device 138 and the battery 44 is being charged, from the transceiver 96 to the transceiver 150 of the charging device 138 by way of UWB wireless communications. The transceiver 150 outputs the received control signal to the signal detector 144 and the determining unit 148.

Based on the supplied control signal, the signal detector 144 detects signals transmitted from the signal generators 122 and outputs the detected signals to the distance calculator 146. Based on the supplied signals, the distance calculator 146 calculates the distance between the radiation detecting cassette 24 whose battery 44 is being charged and the charging device 138, e.g., the distance between the signal generators 122 and the signal detector 144.

The determining unit 148 compares the calculated distance with the distance between the radiation detecting cassette 24 and the charging device 138 at the time the radiation detecting cassette 24 is properly loaded in the charging device 138. If the compared distances match each other and the charging start signal is supplied from the charger 142 to the determining unit 148, the determining unit 148 sends a response signal indicating that the radiation detecting cassette 24 is being loaded in the charging device 138 and the battery 44 is being charged, to the console 28 via the transceivers 150, 96. If the compared distances do not match each other or if the compared distances match each other but the charging start signal is not supplied from the charger 142 to the determining unit 148, then the determining unit 148 sends an error signal indicating that the radiation detecting cassette 24 is not being loaded in the charging device 138 or that the radiation detecting cassette 24 is being loaded in the charging device 138 but the battery 44 is not being charged, to the console 28 via the transceivers 150, 96.

In the radiation image capturing system 10D according to the fourth embodiment, based on the control signal sent from the console 28 to the charging device 138, the signal detector 144, the distance calculator 146, and the determining unit 148 determine whether the radiation detecting cassette 24 is being loaded in the charging device 138 and the battery 44 is being charged, and send, to the console 28, a response signal or an error signal indicative of the determined result. Therefore, the console 28 can easily recognize that the battery 44 of the radiation detecting cassette 24 is being charged by the charging device 138, and also that the radiation detecting cassette 24 can be used for a next surgical operation.

Incidentally, the radiation image capturing systems 10A through 10D according to the first through fourth embodiments are not limited to the aforementioned embodiments, but may be configured as follows.

When the radiation detecting cassette 24 is used in the operating room 12 or the like, the radiation detecting cassette 24 may be subjected to adhesion of blood, contamination, etc. However, when the radiation detecting cassette 24 is designed to have a waterproof and hermetically-sealed structure, and is sterilized and cleaned as necessary, one radiation detecting cassette 24 can be used repeatedly.

The radiation detecting cassette 24 is not limited to use in the operating room 12, and may be used for a medical examination and a round in the hospital.

Also, the radiation detecting cassette 24 may communicate with external devices via optical wireless communication using infrared light or the like, instead of general wireless communication using radio wave.

Figure 16:
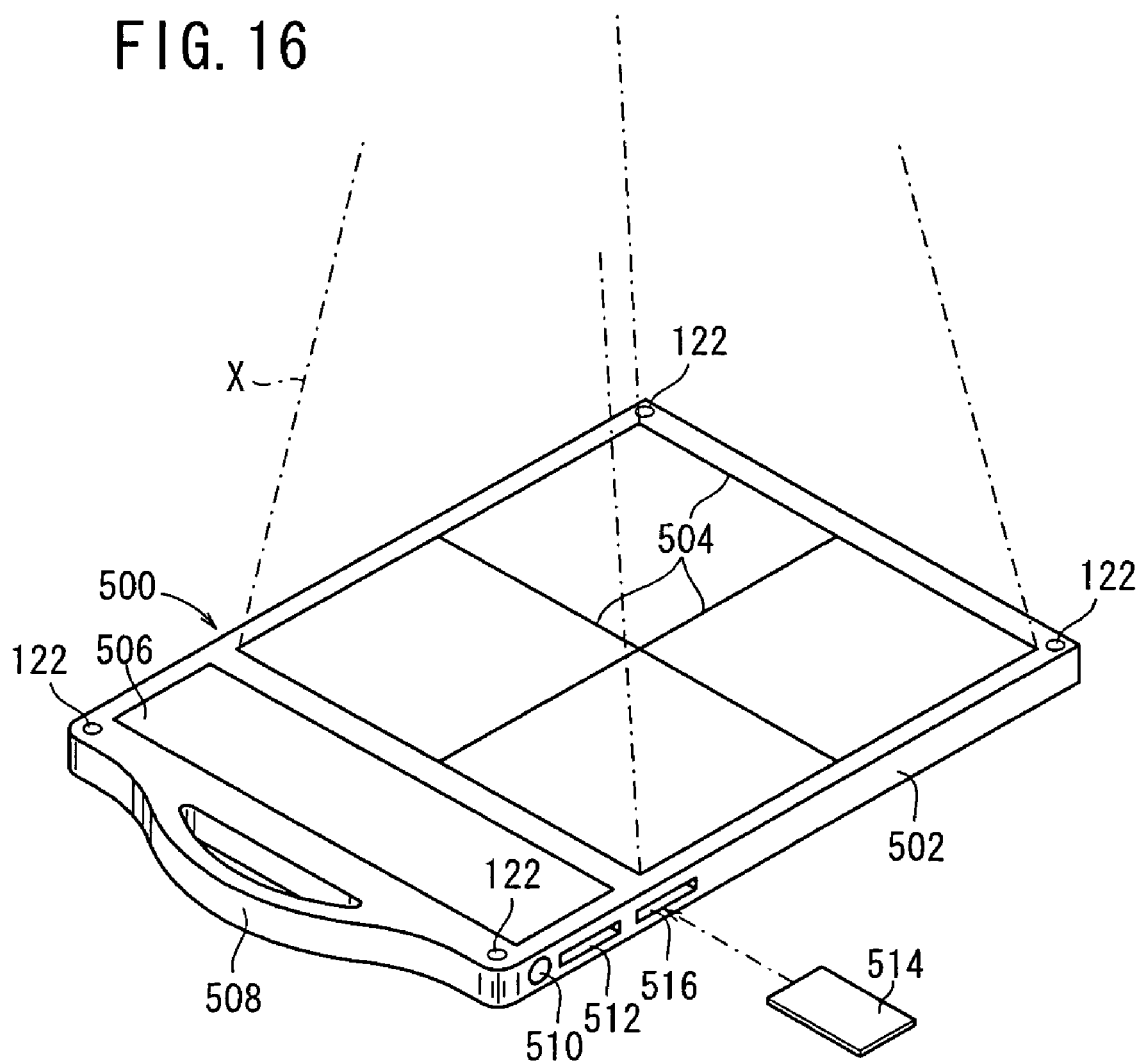
FIG. 16 is a perspective view showing a radiation detecting cassette in the radiation image capturing system according to another embodiment of the present invention.

Preferably, the radiation detecting cassette 500 may be constructed as shown in FIG. 16.

Specifically, the radiation detecting cassette 500 includes a guiding line 504 drawn on the radiation-irradiated surface of a casing 502, the guiding line 504 serving as a reference for setting a captured area and a captured position. Using the guiding line 504, a subject (patient 14) can be positioned with respect to the radiation detecting cassette 500, and an area irradiated with the radiation X can be set, thereby recording radiation image information on an appropriate captured area.

The radiation detecting cassette 500 is provided with a display section 506 on an area thereof other than the captured area, for displaying various information about the radiation detecting cassette 500. The information which is displayed on the display section 506, includes ID information of a patient 14 whose radiation image information is to be recorded on the radiation detecting cassette 500, the number of times the radiation detecting cassette 500 has been used, an accumulated exposed radiation dose, a charging state (remaining battery level) of a battery 44 in the radiation detecting cassette 500, image capturing conditions of radiation image information, and a positioning image of the patient 14 with respect to the radiation detecting cassette 500. In this case, a radiological technician confirms a patient 14 based on the ID information displayed on the display section 506, for example, and also previously confirms that the radiation detecting cassette 500 is placed in a usable state. Then, the technician positions a desired captured area of the patient 14 with respect to the radiation detecting cassette 500 based on the displayed positioning image, thereby capturing appropriate radiation image information.

Also, the radiation detecting cassette 500 is provided with a handgrip 508, whereby it is easier to handle and carry the radiation detecting cassette 500.

Preferably, the radiation detecting cassette 500 may have, on a side thereof, an input terminal 510 for an AC adapter, a USB (Universal Serial Bus) terminal 512, and a card slot 516 for inserting a memory card 514.

When the charging function of the battery 44 in the radiation detecting cassette 500 becomes deteriorated, or when there is not enough time to fully charge the battery 44, the input terminal 510 is connected to the AC adapter to externally supply the radiation detecting cassette 500 with electric power, thereby enabling the radiation detecting cassette 500 to be used immediately.

The USB terminal 512 or the card slot 516 may be used when the radiation detecting cassette 500 cannot transmit and receive information to and from external devices such as the console 28 via wireless communication. Specifically, by connecting a cable to the USB terminal 512, the radiation detecting cassette 500 can transmit and receive information to and from the external devices via wire communication. Alternatively, the memory card 514 is inserted into the card slot 516, and necessary information is recorded on the memory card 514. After that, the memory card 514 is removed from the card slot 516, and the memory card 514 is inserted into the external device, thereby enabling information to be transferred.

A charging device 138 (see FIG. 15) of the radiation image capturing system 10D according to the fourth embodiment may be disposed not only in the operating room 12 but also at a desired place in the hospital. In this case, in addition to charging the battery 44, the charging device 138 may transmit and receive necessary information to and from external devices such as HIS 31, RIS 29, the console 28, etc. by way of a wireless communication function of the charging device 138. The information may include radiation image information which is recorded on the radiation detecting cassette 24 inserted into the charging device 138.

Also, the display unit 140 of the charging device 138 may display necessary information including not only a charging state of the inserted radiation detecting cassette 24 but also radiation image information acquired from the radiation detecting cassette 24.

Further, a plurality of charging devices 138 may be connected to a network. In this case, information about charging states of radiation detecting cassettes 24 inserted in respective charging devices 138 can be collected through the network, and the radiation detecting cassette 24 in a usable state can be located.

As mentioned above, the charging device 138 transmits and receives information with external devices (e.g. console 28) by way of a wireless communication function of the charging device 138. Instead of such a wireless communication function, the charging device 138 may have a wire communication function, by which the charging device 138 transmits and receives information with external devices to obtain the above effects.

Although certain preferred embodiments of the present invention have been shown and described in detail, it should be understood that various changes and modifications may be made therein without departing from the scope of the appended claims.

What is claimed is:

1. A radiation image capturing system comprising:
   a radiation source for outputting a radiation;
   a radiation detecting cassette housing therein a radiation conversion panel for detecting the radiation that has passed through a subject and converting the detected radiation into radiation image information;
   a distance detecting unit for detecting a distance between said radiation source and said radiation detecting cassette;
   a determining unit for automatically determining whether or not the detected distance matches a predetermined distance from said radiation source to said radiation detecting cassette when a radiation image of the subject is captured;
   a warning unit for indicating that the detected distance does not match said predetermined distance if said determining unit judges that the detected distance does not match said predetermined distance; and
   a moving unit for automatically moving said radiation source and/or said radiation detecting cassette to equalize the detected distance with said predetermined distance if said determining unit judges that the detected distance does not match said predetermined distance.

2. A radiation image capturing system according to claim 1, wherein said distance detecting unit comprises:
   a signal generator disposed in either one of said radiation source and said radiation detecting cassette;
   a signal detector disposed in the other of said radiation source and said radiation detecting cassette, for detecting a signal transmitted from said signal generator; and
   a distance calculator for calculating said distance based on the detected signal.

3. A radiation image capturing system according to claim 1, wherein said distance detecting unit comprises:
   a signal generator disposed in said radiation detecting cassette;
   a signal detector disposed in a bed for the subject to lie thereon or in said radiation source, for detecting a signal transmitted from said signal generator; and a distance calculator disposed in said radiation source, for calculating said distance based on the detected signal.

4. A radiation image capturing system according to claim 3, wherein said distance detecting unit detects said distance using magnetism;
said signal generator comprises at least three magnets or magnetic generators disposed in said radiation detecting cassette;
said signal detector comprises a three-axis magnetic field sensor for detecting magnetic fields generated by said magnets or magnetic generators; and
said distance calculator calculates said distance based on the magnetic fields detected by said three-axis magnetic field sensor.

5. A radiation image capturing system according to claim 3, wherein said distance detecting unit detects said distance using an ultrasonic wave;
said signal generator comprises an ultrasonic wave reflector disposed in said radiation detecting cassette;
said signal detector comprises an ultrasonic wave transceiver for emitting an ultrasonic wave toward said ultrasonic wave reflector and receiving an ultrasonic wave reflected by said ultrasonic wave reflector; and
said distance calculator calculates said distance based on a period of time consumed after said ultrasonic wave transceiver emits the ultrasonic wave and until said ultrasonic wave transceiver receives the reflected ultrasonic wave.

6. A radiation image capturing system according to claim 3, wherein said distance detecting unit detects said distance using wireless transmissions;
said signal generator comprises a wireless signal transmitter disposed in said radiation detecting cassette;
said signal detector comprises a wireless signal receiver for receiving a wireless signal transmitted by said wireless transmitter; and
said distance calculator calculates said distance based on a period of time consumed after said wireless signal transmitter sends the wireless signal and until said wireless signal receiver receives the wireless signal from said wireless signal transmitter.

7. A radiation image capturing system according to claim 6, wherein said distance detecting unit comprises a UWB pulse radar for transmitting and receiving UWB wireless signals.

8. A radiation image capturing system according to claim 3, wherein said distance detecting unit detects said distance using wireless transmissions;
said signal generator comprises a wireless signal reflector disposed in said radiation detecting cassette;
said signal detector comprises a wireless signal transceiver for emitting a radio wave toward said wireless signal reflector and receiving a radio wave reflected by said wireless signal reflector; and
said distance calculator calculates said distance based on a period of time consumed after said wireless signal transceiver emits the radio wave and until said wireless signal transceiver receives the reflected radio wave.

9. A radiation image capturing system according to claim 3, wherein said signal generator comprises a composite sensor comprising a geomagnetic sensor, a gravitational sensor, and a three-dimensional gyroscope, disposed in said radiation detecting cassette;
said gravitational sensor outputs the gravitational acceleration of the radiation detecting cassette;
said geomagnetic sensor outputs the direction of geomagnetism;

said three-dimensional gyroscope outputs the attitude of the radiation detecting cassette;
said signal detector detects a detected signal from said signal generator, which represents the gravitational acceleration, the direction of geomagnetism, and the attitude; and
said distance calculator calculates said distance based on the detected signal.

10. A radiation image capturing system according to claim 1, wherein said radiation detecting cassette houses therein said radiation conversion panel, a first wireless communication unit, and a battery for energizing said radiation conversion panel and said first wireless communication unit.

11. A radiation image capturing system according to claim 10, further comprising:
a controller for controlling said radiation source and said radiation detecting cassette; and
an image capturing apparatus having said radiation source and a second wireless communication unit for performing wireless communications with said first wireless communication unit;
wherein said controller comprises:
a third wireless communication unit for performing wireless communications with said first wireless communication unit and said second wireless communication unit; and
an image processing unit for performing a predetermined image processing on the radiation image information which has been transmitted either from said first wireless communication unit to said third wireless communication unit by way of wireless communications or from said first wireless communication unit to said third wireless communication unit via said second wireless communication unit by way of wireless communications.

12. A radiation image capturing system according to claim 11, wherein said radiation detecting cassette further includes a display unit for indicating the position of said radiation detecting cassette based on an indication instruction signal which has been transmitted either from said third wireless communication unit to said first wireless communication unit by way of wireless communications or from said third wireless communication unit to said first wireless communication unit via said second wireless communication unit by way of wireless communications.

13. A radiation image capturing system according to claim 11, further comprising a charging device for charging said battery while said radiation detecting cassette is being loaded in the charging device;
wherein said distance detecting unit further detects a distance between said radiation detecting cassette and said charging device; and
said charging device includes another determining unit for determining whether said radiation detecting cassette is loaded in said charging device or not based on the detected distance between said radiation detecting cassette and said charging device, and outputting a determined result to said controller.

14. A radiation image capturing system according to claim 11, wherein said first wireless communication unit, said second wireless communication unit, and said third wireless communication unit perform UWB wireless communications with each other.

* * * * *